United States Patent [19]
Chubb et al.

[11] Patent Number: 6,129,438
[45] Date of Patent: Oct. 10, 2000

[54] SKIN LIGHT EXPOSURE CONTROL METHODS

[76] Inventors: Charles R. Chubb, 1737 Florine, St. Charles, Mo. 63301; Lisa C. Rottler, 4560 Washington, Florissant, Mo. 63033

[21] Appl. No.: 09/267,955

[22] Filed: Mar. 12, 1999

Related U.S. Application Data

[62] Division of application No. 08/957,686, Oct. 24, 1997, which is a division of application No. 08/572,110, Dec. 14, 1995, abandoned.

[51] Int. Cl.[7] .................................................. F21V 9/02
[52] U.S. Cl. ............................. 362/2; 359/361; 359/596
[58] Field of Search ................................. 359/350, 361, 359/596; 52/200; 362/1, 2; 607/95

[56] References Cited

U.S. PATENT DOCUMENTS

| | | | |
|---|---|---|---|
| 4,128,307 | 12/1978 | Badertscher et al. | 359/596 |
| 5,204,777 | 4/1993 | Curshod | 359/596 |

*Primary Examiner*—Stephen Husar
*Attorney, Agent, or Firm*—Henry W. Cummings

[57] ABSTRACT

A method to improve the probability for good health and decrease the risk of cancer and disease comprising: controlling the indoor spectral radiation environment partial body exposure in an amount above 0.06 MED, but not exceeding 0.2 MED per day by irradiating the body with an artificial light source.

4 Claims, 19 Drawing Sheets

——— AVERAGE FOR OFFICE WORKERS

------- LOW EXPOSURE SUBJECT

DATA: CLIN. & EXP. DERMATOL. 3:77-79;1978
OFFICE WORKER EXPOSURE IN BRISTOL ENGLAND

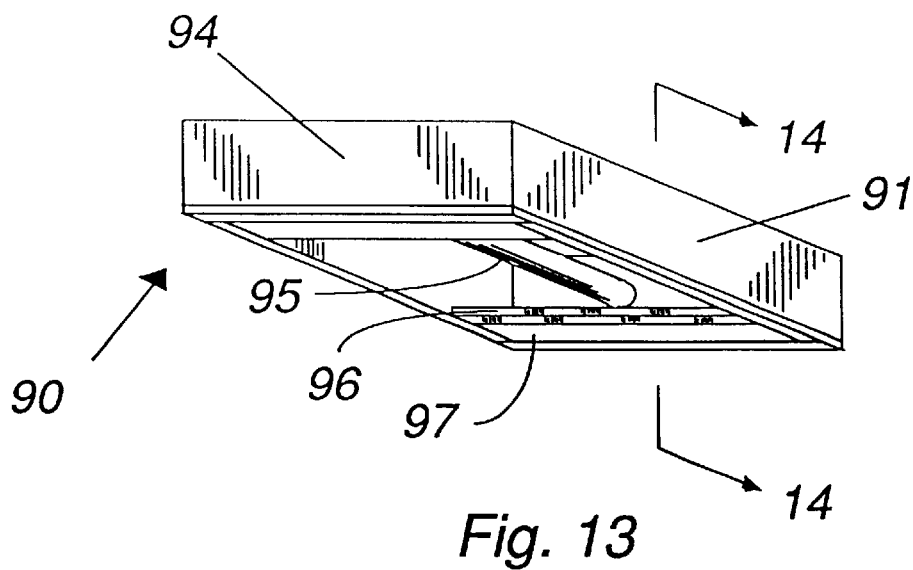
Fig. 13
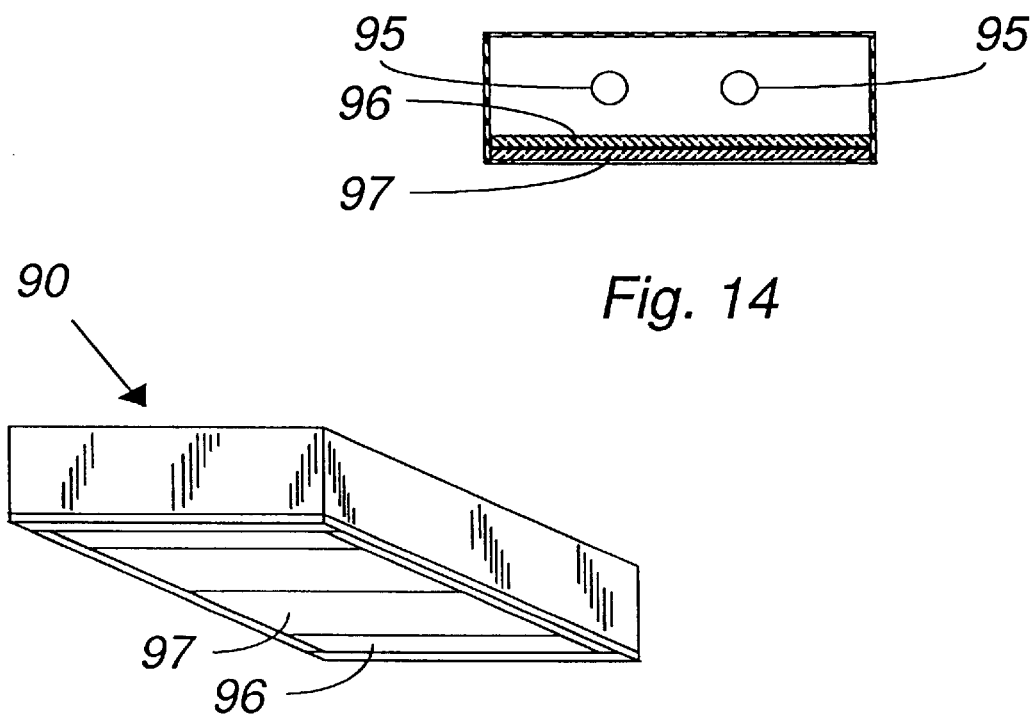
Fig. 14
Fig. 15

SKIN LIGHT EXPOSURE CONTROL METHODS

REFERENCE TO RELATED APPLICATION

This application is a division of application Ser. No. 08/957,686 filed Oct. 24, 1997, which in turn is a division of Ser. No. 08/572,110 filed Dec. 14, 1995, abandoned.

FIELD OF INVENTION

The disclosed invention relates to methods to adjust the light exposure of the skin.

BACKGROUND OF THE INVENTION

Diet, exercise, sleep, genetics and the environment are factors generally recognized as strongly influencing health. Sunlight as a detrimental environmental factor causing skin cancer and other conditions is often discussed. The beneficial effects of sunlight have had much less attention.

For many individuals moderate increases in ultraviolet sunlight exposure as in outdoor work, careful sunbathing or lamp exposure can provide systemic benefits. The output, reduced blood cholesterol, increased liver glycogen stores, reduced blood sugar, increased muscular strength and endurance, increased resistance to infections, increased oxygen carrying capacity of the blood, increased adrenaline in tissues, increased stress tolerance, and increased hormones, Kime, 42.

The purpose of this invention is to provide methods and apparatus to increase the exposure of the skin when the exposure might be deficient such as during dark winter days and decrease the exposure when the exposure might be excessive such as during bright spring and summer days. The proper exposure of skin to solar radiation especially in a changing environment is important to promote health and reduce the risk of disease. An indoor deficiency in ultraviolet B (280 nm to 315 nm) is common. Excessive dietary vitamin D intake with associated problems results from attempts to compensate for the ultraviolet B exposure deficiency. Methods to increase the indoor ultraviolet B (UV-B) exposure to avoid a deficiency in exposure and possible vitamin D deficiency while minimizing the risk of overexposure are included.

Irregular exposure such as excessive weekend and vacation sunlight exposure for persons working indoors during the week is a common problem. Irregular exposure is prevalent in developed countries and is a factor in the increasing incidence of the often fatal melanoma of the skin. Another purpose of this invention is to provide apparatus and methods to obtain a better balance in the day to day ultraviolet exposure of the skin.

Not enough sunlight and vitamin D deficiency can result in poor health and susceptibility to illness. Rickets in children, easy-to-break bones in the elderly, a possible increased susceptibility to some types of cancer, Ainsley, 9, and heart disease, Kime, 42, are typical conditions associated with insufficient UV-B sunlight exposure. The annual health care cost for fractures in the elderly is approximately 10 billion dollars in the U.S. alone, Avioli, 13. Scragg, 70, found coronary heart disease mortality may be associated with vitamin D deficiency (avoidable by sufficient UV-B exposure of the skin).

Sunlight exposure is beneficial for moderating hypertension, high blood sugar and many other conditions, Kime, 42. However, too much sunlight exposure increases the risk of skin cancer and DNA mutations. There is a need to adjust the skin exposure to avoid both insufficient exposure and excessive exposure. The best exposure for an individual varies with skin characteristics. The ratio between too much and too little exposure may be relatively small such as less than a factor of roughly three for face and arm exposure or relatively large such as a factor of 25 for whole body exposure.

Sunlight exposure is related to the important calcium balance. Modern populations have a low calcium diet presumed to result in increased osteoporosis, hypertension and colon cancer, Heaney, 38. The exposure to sunlight can increase the absorption of calcium in the intestine partially counteracting the effects of low amounts of calcium in the diet. Also, sunlight exposure is associated with increased bone mineralization, Kime, 42. Calcium, important in the functioning of cells, interacts strongly with vitamin D (and thus UV-B sunlight exposure), phosphorus, and magnesium. Too much calcium can result in urinary stones and interference with absorption of other essential minerals, Williams, 84. In infancy, excess vitamin D intake may result in hypercalcemia, Oppe, 61.

Vitamin D fortification of many foods is used in the U.S. for protection from rickets and other diseases for those with insufficient vitamin D generated in the skin by ultraviolet B exposure. However, the average person has an intake several times the recommended daily amount. As discussed by Kummerow, 45, and Fraser, 27, an increased mortality and incidence of vascular disease and other conditions may be resulting from high dietary intake of vitamin D. Linden, 49, found myocardial infarction patients had high intakes of vitamin D. Knox, 43, found increased ischemic heart disease mortality for those with high vitamin D intake and also for those with low calcium intake.

Fraser, 27, recommends obtaining the vitamin D from careful sun exposure rather than the diet. Along with obtaining proper exposure of the skin, the diet must be modified to avoid the excess dietary vitamin D intake to obtain the corresponding health benefits. Increased intake of fruits and vegetables tends to reduce intake of other foods with high vitamin D content due to fortification. Although vitamin D is needed primarily in the dark season in northern areas, the extensive fortification is present continuously during the year and is present in the foods for both northern and southern areas.

Historically, problems with insufficient exposure became common in the 1800's in higher latitude cities. With the start of the industrial revolution people moved from farms to cities. The narrow streets and smoke filled sky obscured the sunlight as shown by a photograph of a typical neighborhood, Goldsmith, 32. The incidence of rickets in children increased and this was later found to be due to insufficient ultraviolet B solar radiation exposure. The solar radiation UV-B was obscured both indoors and outdoors. Factory work rather than farm work greatly reduced sun exposure.

Those still involved in farm work tend to have good health for many conditions. The Gambia, is a West African, primarily agricultural country with both men and women cultivating the crops. There is significant outdoor exposure and a mainly vegetarian diet. This country has one of the lowest age standardized cancer incidences in the world. The incidence is more than five times lower than the incidence in the United States. In the U.S., a study in 1941 demonstrated states with a higher percentages of farmers had a trend for lower cancer mortality rates. States with a higher solar radiation index had an even stronger trend for lower cancer mortality, Apperly, 12.

The rickets problem was generally solved by the addition of vitamin D to milk and other foods. However, too much vitamin D may produce toxic effects such as hypercalcemia, Oppe, 61. Excessive vitamin D can be lethal and it is used as a rodenticide, Fraser, 27. Too much vitamin D can cause damage to the arteries. A typical desirable ratio of recommended maximum to recommended minimum dietary intake of vitamin D for infants is a factor of 2.5. Vitamin D generated in the skin by sunlight exposure has the advantage of only small amounts of vitamin D being released. The maximum accumulated amount of sunlight generated vitamin D in the skin is limited reducing the risk of toxic effects. In addition, the deleterious cholesterol in the skin and arterial plaque is reduced by sunlight exposure, Kime, 42. Cholesterol in the skin is converted to vitamin D and other compounds by exposure to UV-B radiation.

The narrow streets and smoke filled sky of the 1800's generally are no longer present. However, the common economic low-melting-temperature window glass blocks most of the ultraviolet B radiation. If one were to photograph the insides of homes and businesses with an ultraviolet B camera, most would be dark to dim just as were the homes and streets of the 1800's. Bare fluorescent lamps without diffuser covers brighten the inside some. Open windows and doors in the spring and fall can brighten the inside of homes in the UV-B just as the mood and spirit brightens in sunny weather. However, now, many homes and workplaces switch from heating to air conditioning with little or no opening of windows in the spring and fall. This leaves an indoor environment with incandescent lighting essentially continually dark in the ultraviolet B spectral region. Hospitals with windows that do not open and fluorescent lighting with prismatic plastic diffusers also are essentially continuously dark in the UV-B.

Those of the elderly who are inside all the time and who do not obtain vitamin D from the diet or supplements can become deficient in vitamin D and develop weak easy-to-break bones. Even in bright countries such as Kuwait, rickets occurs since children spend much of their time inside, Lubani, 51. Dark skinned persons migrating to higher latitudes can encounter vitamin D deficiency problems. Recently, rickets from vitamin D deficiency was reported by Brunvand, 17, for Pakistani children in Oslo, Norway. One approach would be to drink more vitamin D fortified milk to compensate for the lack of vitamin D generated by UV-B irradiation of the skin.

Another approach could be to increase the UV-B radiation indoors by using UV-B transmitting windows or appropriate fluorescent lamps, an object of this invention.

For those who spend significant time outdoors, overexposure can be a problem in the spring and summer on bright days. During this period bare tube fluorescent lamps, Maxwell, 56, open windows, or open doors can aggravate the overexposure problem during long exposure periods indoors. A method of this invention is to move ultraviolet B blocking diffusers over bare fluorescent tubes in the bright season to avoid a possible exacerbation of the overexposure problem.

In cold climates, many persons are deficient in ultraviolet and visible solar radiation exposure of the skin in the winter due to blocking of ultraviolet solar radiation by window glass. Also the clothing worn outdoors in the winter covers much of the skin greatly reducing the exposure. The short length of the day at high latitudes restricts the time available for sunlight exposure. In addition, the low sun angle at midday in the winter at high latitudes reduces the ambient solar irradiation due to the long path length through the atmosphere. These factors make it desirable for some persons to increase the exposure of the skin during the cold dark season. Leach, 46, found office workers in Bristol England receive less than an average of 0.7 mJ/sq. cm. per day of biologically effective radiation, a very low value, in the dark season from November through February, FIG. 1.

In hot climates the skin of many persons is excessively exposed to solar radiation. The long length of the summer day increases the time when solar radiation overexposure can occur. The high sun angle at midday in the summer increases the ambient solar irradiation due to the small amount of scattering and absorption in the short nearly vertical path through the atmosphere. These factors make it desirable for some persons to decrease the exposure of the skin during the hot bright season.

The solar radiation in different spectral regions, UV-B, 280 to 315 nanometers, UV-A, 315 to 400 nanometers, visible light 400 to 700 nanometers and infrared radiation affect various health conditions. There are several suitable window materials such as ultraviolet transmitting glass or plastic with spectral transmission characteristics described by Driscoll, 23, and Sliney, 72. The increased cost of ultraviolet transmitting materials can be partially offset by using a small window orientated toward the sun for transmitting the solar radiation to a room frequently occupied such as a kitchen or living room.

The ultraviolet light rays, UV-B with a wavelength of 280 to 315 nanometers, are beneficial in the production of vitamin D in the skin. However, chronic exposure of untanned skin to ultraviolet solar radiation, especially UV-B, can be associated with DNA damage and an increased risk of skin cancer. Thus, care is needed to obtain adequate exposure in dark seasons and avoid excessive exposure in bright seasons. By reducing the bright season exposure more than the increase in the dark season exposure an increase in the risk of squamous cell skin cancer can be avoided, Lytle 53. By not chronically overexposing untanned skin an associated increase in the risk of melanoma skin cancer and other diseases can be avoided.

Vitamin D deficiency can be a problem for those confined indoors in nursing or other homes with insufficient ultraviolet exposure and a deficiency in dietary vitamin D. In some areas, especially far from the equator, there may not be sufficient sunlight for vitamin D generation in winter months. In addition to latitude, weather affects sunlight availability.

Dietary or tablet supplements are commonly used to avoid vitamin D deficiency. However, there may be problems associated with the use of dietary and tablet supplement vitamin D rather than solar radiation generated vitamin D. Large amounts of dietary or tablet supplement vitamin D can be ingested, however, vitamin D generated in the skin tends to self limit. Accumulated cholecalciferol blocks further synthesis of vitamin D in the skin, Heaney, 38. Fraser, 27, states: "Evidence from domestic animals suggests that persistent feeding of dietary vitamin D may be associated with the development of chronic vascular disease. For this reason alone it is prudent to advise that vitamin D should be obtained from the environment by careful exposure of the skin to solar ultraviolet light rather than from the artificial source of dietary supplements."

Latitudinal variations in incidence and mortality

In addition to rickets and other disorders being associated with vitamin D deficiency, Garland, 29, postulates the increased breast cancer for more northerly, lower-solarradiation areas in the United States may result from reduced solar radiation generated vitamin D. Colon cancer also is possibly associated with vitamin D deficiency by Garland, 30. Ovarian cancer also tends to have lower mortality rates for US women living in areas with more sunlight, Lefkowitz and Garland, 47. For prostate cancer, Studzinski, 77, discusses the studies indicating an increased mortality rate with reduced ultraviolet exposure, increased risk associated with higher serum levels of vitamin D binding protein and decreased risk associated with higher levels of serum 1,25 vitamin D3.

Multiple Sclerosis also has lower incidences in more southerly areas, Mason, 55. Many MS patients were found to be vitamin D deficient by Nieves, 59. Since heat intolerance is associated with MS and many are homebound without sunlight exposure, the deficiency was associated with being a result of the disease rather than a possible cause. However the latitudinal variation being similar to breast and colon cancer indicates vitamin D deficiency, solar radiation or climate induced processes might be considered as a partial cause, risk factor or aggravating factor for increased incidences of the disease. Waksman, 81, recommends influences such as climate, general levels of infection and neuroendocrine processes be investigated. Light induced neuroendocrine effects may be relevant Equatorial regions tend to have low cancer incidences. The hot desert regions near 30 degrees latitude and the colder darker areas beyond 30 degrees latitude tend to have higher incidences for many types of cancer. For the equatorial regions the climate tends to be more uniform throughout the year with the length of days and nights balanced. The warm equatorial temperatures enable more skin to be exposed and the exposure is relatively uniform throughout the year. Also the diet tends to have more fruit and vegetables with low fat intake. The yearly solar radiation tends to be higher in the desert regions rather than at the equator. The fat intake tends to be higher for the developed countries at higher latitudes.

The many high population density areas near the equator tend to result in migration out of the area. The low rate of inward migration leaves a population with skin type well adapted for the local solar radiation environment over a very large number of generations. In lower population density areas at higher latitudes many dark skin persons are living in areas with low solar radiation exposure and many with light skin are living in hot bright climates. Increased migration has resulted in many living in stressful environments. The methods of this invention are directed toward increasing the exposure for those with skin better adapted for brighter environments and decreasing the exposure for those with skin better adapted for a darker environment.

For skin and some other cancers the average incidence decreases with increasing latitude above 30 degrees north. These registries are primarily light skin registries. The higher incidences are in many cases for many persons with light skin living in brighter areas than their ancestors in northern Europe. For squamous cell and basal cell skin cancer the decrease is usually attributed to the lower total solar radiation dose at the higher latitudes. For melanoma of the skin the high incidences are often attributed to chronic exposure of untanned skin. An example is an indoor worker spending a lot of time in the sunlight on weekends and vacations resulting in many sunburns.

Seasonal mortality variations

If insufficient sunlight exposure and associated low vitamin D in the winter is associated with increased risk of diseases such as breast and colon cancer, an increase in mortality in the winter is a possible consequence. For those diseases with increased mortality at higher latitudes with colder darker environments in the winter it might be expected to find an increased mortality in the winter months.

Since respiratory diseases are much more common in the low-temperature low-humidity winter season, increased incidences of other diseases are often considered to be a result of decreased resistance due to the respiratory conditions. The winter increase in respiratory diseases is large as shown in FIG. 2. The mortality values for many other disease categories also are increased in the winter season, but not as much as for respiratory diseases, as illustrated by FIG. 2. The mortality for breast and colon cancer are slightly increased in the winter as shown in FIG. 3.

The seasonal variation of total mortality in Alaska is significantly different than the other states as illustrated by a comparison of FIGS. 2 and 4. In two years shown, 1989 and 1990 there is a narrow winter peak and a wide summer peak as shown in FIG. 4. In earlier years such as 1970 the summer peak is present in the vital statistics mortality tables for Alaska. A possible cause for part of the summer mortality peak, other than ultraviolet exposure, is the reduced melatonin associated with the short summer nights in Alaska. Decreased melatonin resulting from light at night, Blask, 16, has been postulated to be associated with increased disease incidence such as increased breast cancer.

The detrimental effects of short summer nights may be reduced by using room darkening curtains and low temperatures in the bedroom to make it possible to obtain adequate sleep in the summer, not only in Alaska, but in other states as well. Additional factors may be of importance in maintaining a sufficient melatonin concentration and duration. Increased disease incidence from living near electrical power lines or equipment with associated high electric and magnetic fields is believed to possibly be due to suppression of the nocturnal melatonin concentration as measured in animals, Kato, 41.

Mortality and incidence differences for males and females

In many western countries many females have increased sunlight exposure due to not working in an office or factory. Also, clothing styles in many countries tend to have more skin exposed for females than for males such as exposed lower legs for females. For many disease categories such as malignancies, females have lower mortality rates as would be expected if the average exposure is less than the optimum for best health. In some countries, such as Peru and Israel, males have lower malignancy incidence rates than females, WHO, 86, indicating the average exposure may be greater than optimum for females and possibly also for males.

In countries with a clothing style for females with most of the skin covered, the malignancy incidence rates for females is greater than for males such as in some registries in India, Parkin, 62. This indicates a possible underexposure for females. Techniques for obtaining additional private exposure (in conformance with religious beliefs) may offer health advantages for females.

Circulatory disease mortality, countries with and without extensive vitamin D fortification In the U.S. many foods are fortified with vitamin D. In the U.K., France, Belgium, and the Netherlands fortification is used mostly for infants with small amounts for adults. The Netherlands specifically prohibit vitamin D fortification for items other than margarine and infant formulas according to the Tracor-Jitco report, reference FDA, 24. As shown by the mortality trends in FIG. 5, the Netherlands has a low all causes death rate and low circulatory system death rate. Since Fraser has associated dietary vitamin D with vascular disease, the circulatory disease mortality would be expected to be higher in the U.S. than the other countries not having vitamin D fortification for adult high intake dietary items such as bread, breakfast cereal, and milk.

Since there are many differences between the U.S. and the other countries other than vitamin D intake, the mortality difference may be due to other factors. For example, the low circulatory disease mortality rate in France may be partially due to the regular consumption of moderate amounts of wine. However, since data for animals, Kummerow 45, demonstrates the adverse effects of excessive vitamin D, it is reasonable to consider vitamin D as a possible cause for part of the mortality differences.

FIG. 5 shows the generally higher age standardized incidence of circulatory disease in the U.S. compared with the countries without adult dietary vitamin D fortification. Only for the U.K. for the last three periods is the circulatory death rate higher than the U.S. rate. Factors other than the vitamin D fortification may be responsible for the differences but the data indicate a significant fraction of the circulatory disease mortality possibly may be associated with vitamin D fortification.

In the U.K., the dietary intake of vitamin D was estimated to be 116 to 133 IU/day according to the FDA report, 25, by the Fed of Am Societies for Experimental Biology. In 1967 Dale and Lowenberg, 20, estimated the intake for 150 U.S. subjects to be 547 IU/day. As discussed previously, Kummerow estimated the per capita U.S. intake to be about six times the RDA of 400 IU or about 2400 IU/day a very high value. However this value is based on the 10,000 lbs. of vitamin produced in the U.S. Of this 10,000 lbs. only 4000 lbs. was sold in 1969 (Tracor-Jitco report, FDA, 24) so the per capita intake is about 1000 IU/day or somewhat less considering losses in the amount sold prior to intake.

Exposure for Vitamin D generation

The amount of skin exposure needed for vitamin D generation is not great. According to Mary Ellen Siegel, 72, the exposure time required for solar radiation induced vitamin D generation outdoors is only about 15 minutes of exposure of any area every two or three days. About 18 IU/sq. cm. per 3 hour period is generated in skin exposed to sunlight according to Loomis, 50. Thus, for 200 sq. cm. of skin exposed for 0.3 hours, 360 IU of vitamin D, or less due to limiting, would be expected. An ultraviolet transmitting window in a dwelling can provide sufficient exposure at a lower irradiance indoors for a longer exposure period. In a review article Anderson, 11, stated:

"The amount of skin biosynthesis per day is affected by many factors, such as latitude, sun (UV) exposure, dress, season of year, and skin melanin pigmentation. Webb, 82, estimated that only 15 to 20 minutes of exposure of arms and face at midday (c. 2 pm) will yield sufficient skin production of vitamin D sufficient to meet daily needs of adults living in Boston, Mass., USA i.e., 5 micrograms (or 200 IU). In the elderly, however, almost twice as much time is required to yield the same amount of vitamin D production by the skin." These times are only for favorable seasons since Webb, 82, stated in his title: "Exposure to winter sunlight in Boston and Edmonton will not produce vitamin D3 synthesis in human skin."

Exposures measured by Leach, 46, for office workers in Bristol England demonstrate a long period in winter with very low average exposures as shown in FIG. 1. In the winter season dietary vitamin D intake or lamp exposure can be used to obtain sufficient vitamin D. Excess dietary vitamin D intake is a potential problem. In the summer season, care can be used to avoid excess exposure. For office workers, a particular problem is the weekend and vacation exposure of untanned skin which can increase the risk of melanoma of the skin. The exposures for vitamin D generation are low for a person with typical light skin. For those with dark skin higher exposures are necessary.

Whole body exposure has the advantage of a much lower exposure per unit area of skin. This greatly reduces the risk of skin cancer. Also, the cholesterol in the skin and arterial plaque is reduced over a much larger area than the commonly exposed areas such as head and arms. Ainsley, 9, recommends periodic sunbathing for the exposure. This is practical in locations with favorable climate such as parts of California. However in most areas the primary exposure deficiency occurs in the season too cold for outdoor sunbathing. Thus lamps or ultraviolet B transmitting windows are needed. Proper levels of exposure enable reduction or elimination of excessive dietary vitamin D currently being consumed by many individuals and causing adverse health consequences.

Since one MED (Minimal Erythema Dose) whole body exposure produces approximately 10,000 IU, Goldsmith, 32, p. 939 and the adult recommended amount is 200 IU, one MED is a factor of 50 more than needed. For an adult a whole body exposure of $\frac{1}{50}$ MED should be sufficient in the winter in latitudes where an insignificant amount of solar radiation generated vitamin D is produced and a significant amount of vitamin D is not obtained from the diet or supplements.

For the elderly, lactating women and children, the recommended amount 400 IU so the maximum whole-body exposure needed for vitamin D generation for this group is $\frac{1}{25}$ MED. An exposure less than the maximum is needed for those with significant vitamin D from casual solar exposure, the diet and supplements.

Dietary vitamin D intake

According to Kime, 42, the per capita dietary vitamin D intake in the U.S. was 2435 IU per day. Since Kime's value was based on the amount of vitamin D produced and only 40% of the amount produced was sold, FDA, 24, the corrected per capita intake was about 1000 IU/day or less depending on the fraction of the amount sold that was consumed. Dale and Lowenberg, 20, estimated the average daily intake to be 477 IU for older adolescents. Their study did not include adults. The recommended daily intake for adults 25 years of age and older, other than pregnant or lactating women, is a much lower value of 200 IU, Williams, 84. The average U.S. vitamin D intake is higher than the recommended intake for adults by a factor of 2.7 using Dale and Lowerberg's estimate or a factor of 5 using the 1000 IU/day estimate.

According to Kummerow, 45, the vitamin D is added to: " . . . baby foods, imitation dairy products, beverages, sweet sauces, prepared breakfast cereals, margarine, macaroni, noodles, farina, and flour. Most store bread has 250–750 IU/lb. added." The toxic level of 2000–3000 IU per day, Reed, 67, is not extremely high compared to the per capita intake. For infants Sterns, 76, concluded the upper safe level to be between 800 and 1,500 IU per day since intakes in this range result in decreased growth. In addition to the other sources, vitamin D is added to animal feeds and then indirectly consumed in meat and eggs. Vitamin D occurs naturally in only a few food sources such as yeast and fish liver oils, Williams, 84. In countries such as the Netherlands where vitamin D is added only to infant formula and margarine, the age standardized circulatory disease death rate is much less than in the United States. Belgium and France also have low average dietary vitamin D intakes. In these countries the vitamin D is added to only a few food items.

Table 1 includes an estimate of vitamin D using food content data from several sources including Kummerow's values.

TABLE 1

Vitamin D Intake estimate

| Food Item | Consumption lbs./year | Typical content* IU/lbs. | Calculated Intake* IU/day | Estimated Intake** Dale and Lowenberg IU/day |
|---|---|---|---|---|
| Wheat | 111 | 500 | 152 | |
| Other cereals | 22 | 784 | 46 | 0–35 |
| Total rice | 7 | 7 | 0 | |
| Total sugar and sweets | 119 | | | |
| Total potatoes and starchy foods | 100 | | | |
| Total pulses, nuts, seeds | 15 | | | |
| Total vegetables | 206 | 6 | 3 | |
| Total fruit | 156 | | | |
| Cocoa | 3 | 1300 | 11 | 8–38 |
| Beef | 115 | 90 | 28 | |
| Veal | 3 | 90 | 1 | |
| Pig meat (pork and bacon) | 65 | 410 | 73 | |
| Mutton, lamb and goat meat | 3 | 90 | 1 | |
| Poultry meat | 50 | 363 | 50 | |
| Total eggs | 38 | 245 | 25 | |
| Total milk products | 369 | 200 | 202 | 325–387 |
| Cheese (hard) | 13 | 16 | 1 | |
| Cottage cheese | 5 | | | |
| Total fish and crustaceans | 16 | 2700 | 118 | |
| Total oils and fats (fat content) | 54 | 0 | | |
| Margarine (fat content) | 11 | 1900 | 58 | 26–47 |
| Butter (product weight) | 5 | 2700 | 36 | |
| Total: | | | 806 | 477 |

References: Dale and Lowenberg: J. of Pediatrics, 70:952–955;1967
OEDC (Organiz. Econ. Coop. & Develop.), Food Consumption Statistics, Paris, 1978
Kummerow: Am. J. Clin. Nutr, 32:58–83;1979
Kummerow: Am. J. Clin. Nutr, 29:579–584;1976
Wilson, Principles of Nutrition, Wiley, 1975. p486
Pennington, Food Values of Portions Commonly Used, 15th Ed. 1989.
Mutton, lamb and goat estimated using beef content value
*For choice of food items with high vitamin D content.
**Catagories not listed: Diet foods 0–20 IU/day; Natural foods 20–66 IU/day.

A vitamin D intake from bread, meats other than lunch meat, poultry, and fish are not included in the table by Pennington, 64. If a person eats bread fortified with vitamin D the intake can be high. If a person eats a high percentage of lunch meat the vitamin D intake can be high as indicated by the values in Pennington's table. If other meats have a high content as measured by Kummerow, the vitamin D intake can be high. If vitamin D rich fish is consumed the intake can be high. If breakfast cereal fortified with vitamin D is used the intake can be high. If fortified margarine and butter are used the intake can be high. The combination of these items results in an estimated intake of over 800 IU per day as listed in table 1. This large value is not greatly less than the 1000 IU per day value derived from the amount of vitamin D that was sold in one year.

Many persons can have an intake of vitamin D higher than the average due to variations in dietary habits and the use of vitamin pills. Intake of toxic levels of vitamin D may be having serious consequences for large numbers of persons. Excess vitamin D from the diet may result in precipitation of calcium salts in the kidneys and arteries resulting in irreversible kidney damage and calcification of major arteries. Sunlight exposure to obtain vitamin D rather than obtaining the vitamin D from the diet has the advantage the exposure may result in added calcium to increase bone mineral density resulting in stronger bones. Also, a reserve supply of calcium in the bones is obtained for use during any periods when there may be a net loss of calcium.

Licht, 48, provides an ancient history reference to long term sunlight exposure of shaved heads resulting in increased skull mineralization in comparison with those with less long-term sunlight exposure due to headwear and hair covering. The increased skull mineralization decreases the transmitted light to the outer layers of the brain and acts in a manner similar to the tanning of the skin to protect underlying tissues. Increased bone mineralization may also serve to protect the bone marrow and blood forming processes. A rapidly changing environment such as a vacation to a sunny beach area does not allow time for protective mechanisms such as bone mineralization in addition to tanning to operate. This raises the possibility of light overexposure affecting disorders other than just the skin.

The calcium for increased mineralization is supplied by increased ultraviolet light resulting in higher dietary calcium absorption in the intestine. Kime, 42, described an experiment comparing fluorescent lamp lighting resulting in increased calcium absorption while incandescent lighting resulted in decreased calcium absorption for two groups of veterans living indoors in a soldiers home in Chelsea, Mass.

Vitamin D in animal rations

The control of the inside optical radiation environment for farm animals is desirable to enable the use of less vitamin D in animal rations. Reduced vitamin D in animal rations decreases the vitamin D intake of humans consuming meat. For those persons with excess vitamin D intake a reduction in vitamin D consumption may result in improved health and extended life span.

By using adjustable ultraviolet solar radiation from skylights in farm buildings it may be possible to reduce the amount of vitamin D in animal feed without reducing the food productivity. For a skylight, an additional outer reflecting section may be necessary to prevent excessive heating from the greenhouse effect for hot days. The overall reduction in the fortification of foods to reduce the per capita consumption to a value near the recommended daily allowance may have potential to significantly improve health. Obtaining more vitamin D from ultraviolet skin exposure and less from dietary intake appears to be desirable as long as great care is taken in avoiding skin overexposure as discussed by Fraser, 27.

Antioxidants

When using increased skin exposure in place of dietary vitamin D, antioxidants in the diet have increased important. According to Shigenaga and Ames, 71, the oxidant singlet oxygen is generated from oxygen by the absorption of energy from a dye activated by light. They also point out: "It has been estimated that approximately 30% of all cancers are related to the diet and that the main culprit is a dietary imbalance of too few fruits and vegetables and too much fat."

The antioxidants Vitamins C, E and beta carotene provide resistance to some of the adverse effects of exposure. Thus, fresh fruit and vegetables containing antioxidants are important to include in the diet to reduce DNA damage. The use of as grown food in place of processed foods such as some breakfast foods and prepared frozen foods has other health advantages such as reduced trans fatty acid intake. Since DNA absorption and vitamin D formation in the skin have similar action spectra, care in skin exposure along with the diet is necessary to reduce the risk of excessive unrepaired DNA damage.

Beneficial effects of sunlight other than vitamin D formation

Solar radiation exposure has many other beneficial health effects besides the beneficial influences on vitamin D generation. The Maryland Heart Association found sunbathers suffer from hypertension only half as much as the general population, Kime, 42.

The exposure of the skin to an appropriate amount of blue or green light is beneficial to detoxify and stimulate the elimination of a natural metabolite, bilirubin. In the absence of light, bilirubin has to be conjugated with glucuronic acid or other sugars to be excreted effectively, McDonagh, 57. An example of the beneficial use of increased skin illumination using blue or green light is the phototherapy used for treating neonatal jaundice.

Seasonal affective disorder, SAD, is another condition treated using visible light. In dark seasons, bright artificial lights are used during reading or in the viewing direction to moderate or eliminate depression.

The nocturnal melatonin concentration depends on the circadian rhythm determined by the light variation between night and day. As discussed by Blask, 16, a high melatonin concentration may be important for low incidence for several types of cancer. Blocking the early morning sunlight in the summer by shades at windows may provide a health benefit by extending the nocturnal period of high melatonin concentration. Avoiding late night activities such as television viewing also may extend the period of high melatonin concentration.

Further, certain skin diseases, such as psoriasis and vitiligo among others may be partially alleviated by exposure to sun light or ultraviolet radiation, UV-A, with wavelengths between 315 and 400 nanometers, Bortnick, 1. Consequently a window of light transmitting material or lamp allowing the irradiation of skin may aid in the treatment and prevention of these and other diseases.

Possible detrimental effects of sun or lamp exposure

In addition to these beneficial effects of solar radiation exposure there are many possible detrimental effects of excessive skin exposure.

Nonmelanoma skin cancer from excessive accumulated solar radiation exposure has a very high incidence. In 1977–78 the number of new cases per year was over 2 per 1000 persons, WHO, 85, page 139. Nonmelanoma skin cancer does not have a high fatality rate similar to the lower incidence melanoma of the skin, however the incidence of melanoma of the skin is increasing in many areas such as Australia.

Simone Harrison, 36, found rapid development of melanocytic nevi during childhood in Australia. A large number of melanocytic nevi is a risk factor for melanoma skin cancer. Very high counts in the study in Australia were associated with estimated sun exposures of four or more hours per day. For light skinned persons in bright environments such as Australia, ultraviolet transmitting windows may not provide an advantage for much of the year. If an advantage is provided it may be for only a few brief periods.

Mangus, 54, postulated the increasing incidence of melanoma of the skin in the Nordic countries is associated with changing clothing styles and vacations. The changing clothing styles result in increased skin exposure on bright spring and summer days. Vacations to more southerly latitudes result in exposure of untanned skin to a bright solar radiation environment. A more uniform exposure to ultraviolet radiation throughout the year using UV transmitting windows may provide many health benefits without the detrimental effects associated with brief vacations to bright areas or utilization of tanning booths. Infants and children in strollers without sunshades may be subjected to overexposure especially if exposed for long periods in midday during bright summer days. Irregular exposure, being indoors much of the time, followed by a day with lots of outdoor exposure is very undesirable and a risk factor for melanoma of the skin. In the darker times of the year there is the opposite problem of obtaining sufficient exposure with the many associated beneficial effects.

Conditions other than skin cancer may have an increased risk resulting from solar radiation overexposure in bright seasons. Immune system suppression by ultraviolet radiation, Goettsch, 31, may result in increased incidences of many types of immune system related conditions. Also, ultraviolet radiation can activate the human immunodeficiency virus-1 promoter, Valerie, 78, or the virus, Stanley, 75. Effects of multiple ultraviolet exposures on transcription induction from the long terminal repeat of the human immunodeficiency virus were measured by Schreck, 68.

As discussed by Nowak, 60, the HIV virus may overcome the immune system by many mutations developing a resistant strain of the virus. The avoidance of excess mutation inducing ultraviolet exposure by those who are HIV positive may extend the latent period. Cebula, 19, describes techniques to compare lamps for selection of lamps with minimum mutagenic effects. However, ultraviolet exposure is associated with strengthening of some of the properties of the immune system. As listed by Hawk, 37, excess ultraviolet exposure can exacerbate viral infection. Until it is determined whether or not the latency period is dependent on ultraviolet exposure, it is unknown if the lamp exposure will be detrimental, beneficial or not have an effect for those who are HIV positive. Ultraviolet-B phototherapy has not demonstrated adverse short term effects for 28 HIV positive patients, Fotiades, 26. If sunlight induces the progression of AIDS, Vincek, 80, hypothesizes TNF alpha (tumor necrosis factor-alpha) and cis-UCA (urocanic acid) released by intense sun exposure can accelerate the onset and progression of AIDS in HIV-infected individuals.

Relevant patents

The many advantages of obtaining sufficient exposure in the dark seasons and avoiding excessive exposure in the bright seasons demonstrate the need for methods and apparatus to assist in obtaining proper exposure. There are existing patents of use in conjunction with the present invention to achieve improved exposure of the skin.

The patent by Bortnik, U.S. Pat. No. 4,546,493, refers to tan through garments. The types of materials used can be irritating to the skin. By using windows in conventional garment material the possibly irritating material can be offset from contact with the skin to reduce the possibility of irritation. This material can provide needed additional skin exposure in dark seasons.

The patent by Calverley, U.S. Pat. No. 5,206,229, describes vitamin D analogs for pharmaceutical use. The disclosed invention refers to methods to obtain benefits by the use of ultraviolet induced vitamin D.

The patent by Fiorenza, U.S. Pat. No. 4,656,778, describes a three track storm window. By use of a ultraviolet transmitting window in one (the outer) of the three tracks and ultraviolet blocking windows in the other two tracks, a window with adjustable ultraviolet transmission can be obtained.

The patent by Ryan, U.S. Pat. No. 5,196,705, describes an exposure meter that can be used to adjust the ultraviolet transmission for an appropriate exposure either higher or lower.

The patent by Rattray, U.S. Pat. No. 4,843,279, describes a fluorescent lamp that can be used to obtain high levels of adjustable ultraviolet radiation exposure in the disclosed fixture with adjustable ultraviolet transmission.

The patent by Pepall, U.S. Pat. No. D282,58 1, describes a sunlamp that can be used with the disclosed adjustable ultraviolet transmission devices to obtain an appropriate ultraviolet exposure.

The patent by Dalebout, U.S. Pat. No. 5,000,444 describes a dual action erercise cycle with air resistant blade members in back. This exercise cycle is particularly well suited for the addition of irradiation lamps in back. The air blades provide air circulation for cooling of the seated individual. The air cooling helps to compensate for the additional heat from the lamps.

The patent by Young, U.S. Pat. No. D310,878 describes a tanning station for use with exercise devices. The irradiation devices of this invention typically use lower irradiances with doses less than the level for tanning. The irradiation devices of this invention are selected for vitamin D formation and potential reduction of risk of particular types of cancer, heart disease and other conditions. Tanning lamps commonly use predominantly ultraviolet A irradiation. For vitamin D generation in the skin ultraviolet B radiation is normally utilized.

OBJECTS OF THE INVENTION

The primary object of the invention is to provide a method and apparatus to adjust the exposure of the skin to optical radiation.

Another object is to obtain a skin exposure favorable to good health and avoidance of disease.

A further object is to provide a skin exposure for formation of an appropriate amount of vitamin D in the skin so excessive vitamin D in the diet can be reduced or eliminated.

An additional object of the invention is to maintain the warmth and comfort in cold environments provided by similar devices without adjustable features.

Still another object of the invention is to provide a device that is durable, easy to adjust and has a pleasing appearance.

Yet a further object of the invention is to provide an adjustable device that may be used in the treatment of skin diseases for which exposure to optical radiation is beneficial.

Another object is to provide a method and apparatus to adjust the internal ultraviolet, visible and infrared radiation environment to levels suitable for an individual with particular skin characteristics.

An additional object is to provide a method and apparatus to adjust the inside optical radiation environment for an improved balance through the changing seasons.

Another object is to provide a method and apparatus to keep the skin irradiance low to keep the risk of detrimental effects, including skin cancer, low.

Another object is to provide a method and apparatus to have whole body radiation to reduce the cholesterol in the skin, artery plaque and other tissue.

Another object is to provide a method and apparatus to have whole body radiation to generate vitamin D at the lowest possible irradiance (to keep the detrimental effect risk low).

Another object is to provide a method and apparatus to have whole body radiation over a long time period to allow the body blood pool to circulate through the irradiated skin.

SUMMARY OF THE INVENTION

Some or all of these objectives can be achieved by using an ultraviolet transmitting window or lamp for simulated sunbathing in dark seasons for persons needing additional exposure. This makes it possible to reduce or eliminate the need for dietary vitamin D with potential associated problems. Care in bright season exposure enables the yearly exposure to be reduced even with increases in dark season exposure. The intake of five servings of fruits and vegetables, low in vitamin D content, each day helps to reduce the intake of the many other foods with high vitamin D content for persons with excess vitamin D intake.

The use of a lamp in the bathroom enables whole body irradiation during bathing without requiring additional time for a person with a busy schedule;

The bathroom is the room often kept warm enough for an unclothed person in cold areas far from the equator;

The use of an adjustable lamp, such as by an adjustable window in front of the, lamp, or less time, allows a reduced exposure during spring and fall seasons when sunlight exposure and diet provide part of the recommended daily allowance of vitamin D.

Exercise clubs, gymnasiums and indoor swimming pools are areas where clothing exposing more skin than usual is worn. These areas offer opportunity for closer to whole body irradiation during the dark seasons. The benefits of exercise are obtained and the exposure is achieved at the same time without requiring additional time for busy persons.

Exposure values needed in dark seasons for some persons

If a lamp is used to provide additional vitamin D, then the amount needed is determined from the difference between the recommended amount and the amount from solar radiation generation, the diet and supplements. The MED varies between individuals being low for light skin persons and high for dark skin persons. For example, Westerhof, 82, lists some typical values for 17 individuals ranging from 30 mJ/sq. cm. to 381 mJ/sq. cm., using a 20 nm wide (halfwidth) filter centered at 298 nm for the UV-B measurements and mercury arc lamp simulating the solar spectrum. Berger, 17, describes other lamps for simulating the solar spectrum for MFD measurements. These lamps also can be used for stimulating vitamin D generation in the skin.

Since outdoor workers have lower mortality rates than indoor workers, exercise and an increased exposure for indoor workers may improve health. Outdoor workers obtain an exposure of about 10% of the ambient environment while indoor workers obtain about 3% for a weekly average, WHO, 85. The exposure of office workers could be increased by a factor of about 3.3, along with increased exercise, and an overall improvement in health may be achieved.

Overall, there is a need for an appropriate level of skin irradiation for various wavelengths to obtain beneficial effects for health. A deficiency in exposure may occur especially for dark skin persons in cold dark seasons. There is a need to have moderation in the exposure and avoid overexposure especially in hot bright seasons for light skin persons. There is a need for balance in the exposure through the seasons, particularly in the latitudes with large fluctuations in the environment.

As there is a need for recommended daily allowances for different diet items without excesses, there is a need for an appropriate daily skin irradiation for different wavelengths without excessive overexposure. Preferably the ranges are 0.02 MED for whole body exposure to 0.2 MED for 10% of whole body exposure for vitamin D generation. Multiple exposures over one MED greatly increase the risk of skin cancer. The minimum dose requirement established by the Health Council of the Netherlands, 1986, World Health Organization, 85, is 55 MED per year or about 0.15 MED per day. This value is slightly less than the above value of 0.2 MED per day value for a person with 10% whole body exposure. In a preferred embodiment the range for partial body exposure is from more than 0.06 MED to not more than 0.2 MED per day.

Relative to the amount of energy for longer wavelengths favorable for use with the UV-B exposure, one study was conducted for light exposure effects on carbohydrate metabolism. Pincussen, 65, found the relative energy in the ultraviolet and visible regions in sunlight produces favorable maximum ratios of glucose to lactic acid in the blood and maximum ratios of glycogen to lactic acid in the liver and muscle in animal carbohydrate metabolism experiments. By use of the sunlight spectrum the exposure energy for longer wavelengths can be estimated. These exposure values can then be modified as necessary for special purposes and individual requirements.

Using the relative energy in sunlight for different wavelengths on clear days with the sun near the zenith, the doses for the UV-A, and the visible and IR irradiation can be estimated. For sunlight, the UV-A dose is roughly 30 times the UV-B dose. The visible and IR dose is roughly 20 times the UV-A dose.

Typical outdoor summer exposure rates measured by Diffey, 22, for light skin persons range from less than 0.01 MED per hour walking in the shade to 0.24 MED/hour while walking on a beach on a cloudy day to as high as a maximum value of 2.3 MED/hour while driving a car with the windows open.

An exposure of 1 MED in a day indicates the normal capability of the skin to repair the damage is exceeded representing an overexposure. For persons with conditions such as xeroderma pigmentosum with defective DNA repair capability, or sarcoidosis, Bell, 15, exposure requires special precautions.

One technique to av o id excess exposure in the summer is to use care in staying out of the direct sunlight when the shadow is shorter than the height of a person. This provides a sun protection factor of about 2.7 or greater due to the long path length through the atmosphere compared with the time when the sun is near the zenith and when shadows are short. One factor to help keep the risk of squamous cell carcinoma skin cancer low is to maintain a low total yearly exposure (total MED's), Lytle, 53.

One factor to help keep the risk of melanoma skin cancer low is to avoid chronic exposure of untanned skin. An example is avoiding getting many sunburns or high doses on vacations or weekends while being inside much of the time during the week.

Use of lamps for exposure in dark seasons

Since MED's range from about 30 to 381 mJ/sq. cm., an exposure of 1/50 MED for whole body exposure ranges from about 0.6 mJ/sq. cm. to 6.3 mJ/sq. cm. for light skin persons to blacks. For a 1000 second (17 minute) exposure the corresponding range in irradiance is: 0.6 microwatts/sq. cm. to 6.3 miicrowatts/sq. cm. According to Maxwell, 56, fluorescent lamps produce up to about 0.14 microwatts/sq. cm. (0.0070 mnicrowatts/sq. cm. nm*20 nm) at a location where the illuminance is 500 lux. Thus a single bare tube fluorescent lamp (with a high UV output) may be suitable for generating roughly 25% of the recommended daily vitamin D for a light skinned person during a 17 minute period of whole body exposure. To provide a higher percentage of the recommended daily vitamin D, a filter for the visible light that transmits the ultraviolet B radiation can be used to enable additions lamps to be used without excessive brightness.

Some quartz halogen lamps produce 0.2 microwatts/sq. cm. of effective ultraviolet radiation and greater at a distance of 30 cm., WHO, 85, page 227. Thus, these lamps in addition to fluorescent lamps are suitable for stimulation of vitamin D formation in the skin.

For a precise evaluation of the percentage of the recommended vitamin D provided by a lamp the spectral variation of the MED, Parrish, 63, and the lamp spectrum can be used. Lamp spectra and the MED both vary greatly with wavelength in the UV-B spectral region.

The times of the year when there is a deficiency in exposure has not been measured extensively. Leach, 46, measured the exposure throughout the year for office workers in Bristol, England, FIG. 1. He found average daily values of less than 1 millijoule/sq. cm. in the winter and greater than 8 millijoules/sq. cm. in the summer. For a light skinned person with an MED of 30 millijoules/sq. cm. a 0.2 MED exposure for 10% whole body exposure is 6 millijoules/sq. cm. In Bristol, for office workers, the exposure was over 6 millijoules/sq. cm. only for weeks approximately 21 through 34. Since vitamin D tends to accumulate over many days the vitamin D may be sufficient over more than the 13 weeks in the hot season. However, the need for additional exposure in the large number of remaining weeks is evident if excess dietary vitamin D intake is to be reduced.

For locations at lower latitudes a longer period with daily exposure over 6 mJ/sq. cm. is usually expected. For these areas the number of weeks with low exposure is correspondingly reduced. For very bright areas the ambient solar radiation exposure may be sufficient for the entire year. However, even with sufficient sunlight, if there are not sufficient outdoor periods while wearing suitable clothing the skin exposure may still be deficient.

The sufficiency of the combined effects of exposure and dietary vitamin D intake is indicated by the circulating vitamin D in the blood. The levels of a primary vitamin D component in the blood, 25-OHD, were measured throughout the year in Denmark by Lund, 52. The summer levels are about 13 ng/ml greater than the winter levels. In the U.S. the summer levels are about 12 ng/ml greater than the winter levels for indoor workers, Neer, 58. The dietary vitamin D intake in the U.S. is very high and the average annual 25-OHD levels range from about 40 ng/ml for persons in the north, Seattle and Boston, to over 80 mg/ml for persons in the far south, Palm Beach, ibid. In France, were vitamin D is added to only a few food items, the average 25-OHD levels were found to be 10 ng/ml to 20 ng/ml by Bayard, 14.

Levels of 2 to 7 ng/ml are associated with rickets as shown by the observations of Bayard. In a case control study in Auckland, New Zealand Scragg, 70, found the risk of myocardial infarction for a group with plasma 25-OHD levels above the median level of 12.3 ng/ml was only 43% of that of the control group. Garland, 30, recommends a 25-OHD level of 27 to 41 ng/ml to maintain a low risk of colon cancer.

The current average levels of 40 ng/ml to over 80 ng/ml in the U.S. with a decrease to about 34 ng/ml to over 74 ng/ml in the winter (6 ng/ml less than the average, half the winter to summer variation of 12 ng/ml) are well above the levels to reduce the risk of rickets, myocardial infarction and colon cancer in the winter. A concurrent decrease in dietary vitamin D, increase in winter skin exposure and decrease in summer exposure to maintain the 25-OHD levels above 27 ng/ml may retain the current advantages for rickets, myocardial infarction and colon cancer and in addition provide the many potential health improvements associated with reduced dietary vitamin D excesses.

Considering the upper limit for 25-OHD, Garland, 30, recommends an upper limit of 41 ng/ml and Jacobus, 40, recommends an upper limit of 80 ng/ml. Garland as previously discussed recommends a range of 27 ng/ml to 41 ng/ml for maintaining a low risk of colon cancer. The normal range of 25-OHD listed by Jacobus, 40, is 22 to 200 nmol/liter (8.8 ng/ml to 80 ng/ml). The upper limit for the normal range is thus 80 ng/ml. Hypervitamintosis D was associated with drinking milk with excessive vitamin D for eight patients by Jacobus, 40. The average 25-OHD levels for each of the eight patients ranged from 83 ng/ml to 665 ng/ml. The range recommended by Garland provides a safety factor of about two below the hypervitamintosis D lower limit. The measurement of 25-OHD provides a convenient means to experimentally verify the satisfactory functioning of exposure lamps and outdoor exposure habits in maintaining recommended vitamin D levels.

Since part of the effectiveness of vitamin D is in controlling the important calcium balances, sufficient dietary calcium is necessary. This is not a common problem in the U.S. However in some countries, and for some with unique dietary habits such as strict vegetarian, the calcium intake can be important as discussed by Prentice, 66. Low vitamin D intake along with low ultraviolet B skin exposure results in loss of calcium. Davies, 21, found large negative calcium balances (net loss of calcium) with the fecal output of calcium nearly doubling by 61–70 days after start of a confined environment experiment of nine young male volunteers with the low dietary vitamin D intake characteristic of the British diet and without ultraviolet B skin exposure.

The August exposures for office workers in Bristol, 8 mJ/sq. cm. per day measured by Leach, 46, and the August 25-OHD levels for British subjects, Stamp, 74, about 20 ng/ml, can be used to estimate required lamp exposures. In Britain the average vitamin D intake is about 150 IU/day. Relative to the adverse effects of vitamin D this intake has an advantage over the much higher average intake levels in the U.S. To achieve the 25-OHD level of 27 to 41 ng/ml recommended by Garland, 30, the estimated exposure range for a clothed individual using the 8 mJ/sq. cm. and 20 ng/ml is: 11 to 16 mJ/sq. cm. per day. If the effectiveness of whole body exposure to a clothed person exposure is ten to one then the estimated lamp exposure for whole body exposure is 1.1 to 1.6 mJ/sq. cm. per day. For a person with an MED of 30 mJ/sq. cm. the range is 0.036 to 0.053 MED's.

The average ambient radiation for Bristol England is roughly 900 mJ/sq. cm. per week according to the measurements of Leach, 46. For Washington, D. C. the ambient solar UV (299 nm) is listed as 1,890 kJ/sq. m. per year by Lytle, 53. The corresponding average daily values of 129 mJ/sq. cm. for Bristol and 518 mJ/sq. cm. for Washington, D.C. differ by a factor of four. Increased cloudiness and the higher latitude of Bristol results in an expected lower average ambient ultraviolet erythemally effective radiation for Bristol. The use of lamp exposure in the dark season is thus more important in the more cloudy higher latitude areas.

If the exposure is kept below 0.053 MED's per day and the lamp is used for the dark half of the year, then the yearly dose is less than 10 MED's. Since the estimated lifetime average dose for mid-latitude areas in the U.S. such as Washington, D.C. is 85 kJ/sq. m. per year, Lytle, 53, the average daily dose is about 23 mJ/sq. cm. An increase in dose of 1.6 mJ/sq. cm. is a 7% increase relative to a daily average of 23 mJ/sq. cm. Since lamp exposure is needed for only about half the year, the yearly dose is increased by 3.5%.

To avoid an accumulated yearly increase in dose, the summer exposure must be correspondingly reduced. Since the summer exposure is at such a very high rate with time for bright clear days only a small reduction in bright day exposure can compensate for the increased winter exposure. An exposure period of 140 seconds (2.3 minutes) of clear midday outdoor July erythemally effective ultraviolet radiation (0.02 mJ/sq. cm.) is equivalent to a typical indoor workday eight hour fluorescent lighting exposure of 2.8 mJ/sq. cm.

Lamp and window characteristics other than exposure values

In addition to selecting the lamp and outdoor exposure to obtain a recommended 25-OHD level other details of lamp selection are important.

For eye protection during indoor exposure it is desired a lamp be mounted high with low reflecting surfaces to keep the retinal irradiance in the UV blue region low. To irradiate a large fraction of the body it is desired the lamp be placed at an angle rather than directly overhead. To avoid eye irradiation and irradiate a large fraction of the body the lamp might be placed upward toward the ceiling relative to the standing position in a shower or in front of a mirror.

In bedrooms and hospital rooms, indirect visible lighting with a shaded lamp on the wall irradiating the wall and ceiling over the top of the head of a reclining person is desirable for eye comfort. Since most materials have a low UV-B reflectivity the UV-B irradiation for a reclining person can be directed toward the preson from an over-the-head wall location.

There are advantages to have vitamin D generation by light exposure rather than obtaining vitamin D from the diet or supplements. In areas not too far from the equator where sufficient sunlight is available year round a bathroom window, other room window, door or skylight with adjustable UV transmission offers a potential lower cost than a lamp requiring electrical power use.

A UV transmitting skylight can provide a higher room irradiance for indoor sunbathing in cool weather than a window with perpendicular farther in angle from the sun direction when the sun is high in the sky (the time of greatest UV transmission through the atmosphere). The use of a skylight in a bathroom enables whole body irradiation during the periods when clothes do not usually cover most of the skin.

Cholesterol

Kime, 42, describes how plaque in arteries is reduced by sun exposure of the skin. First, the cholesterol in the skin is reduced by light exposure converting the cholesterol to vitamin D and other compounds. When the cholesterol in the skin is maintained low for a long period using the light exposure the plaque in the arteries begins to decrease. High blood pressure associated with the plaque decreases as the plaque is removed.

To obtain reduced plaque in the arteries and the potential heart disease risk reduction associated with plaque reduction it may be necessary to avoid excessive dietary cholesterol. As pointed out by Kummerow, 45, some areas such as rural Romania have much higher dietary cholesterol intake than the U.S. yet the rate of myocardial infarction is much lower than in the United States. The increased sun exposure in rural areas may be effective in maintaining a low level of cholesterol in the skin and a corresponding low level of plaque in the arteries.

In experiments with rabbits, Altschul, 10, demonstrated serum cholesterol and arteriosclerosis could be reduced by ultraviolet irradiation of the skin.

To reduce coronary heart disease mortality, cholesterol reduction by diet modifications and drugs have been successfully used as discussed by, Gould, 34. Since total mortality is not reduced in the same manner as coronary heart disease mortality there is the question of whether or not lower cholesterol is associated with higher mortality for conditions other than coronary heart disease. Golier, 33, analyzed multiple studies and found for men, increased suicide is associated with lower levels of cholesterol.

Moderate sun exposure to reduce cholesterol in place of diet and drug techniques may not have the disadvantage of possible increased mortality from suicide since moderate light exposure is often relaxing and is used to reduce or eliminate depression.

Reduction in exposure in bright seasons

In many areas overexposure in bright seasons is a growing problem as indicated by the increasing mortality from melanoma of the skin. Chronic exposure of untanned skin and many sunburns are risk factors for melanoma of the skin. Summer exposure on weekends while being inside the rest of the week and vacations to brighter areas can be associated with increased risk of melanoma of the skin.

For a person with sensitive skin the number of MED's in a three hour exposure in midday is as high as 15 at the equator and 10 at 40 degrees latitude, WHO, 85, table 3.3. By staying out of the direct sunlight when the shadow is shorter than the person is tall the protection factor is 2.7 or greater, Holloway, 39. The shadow rule for solar UV-B protection is: sunburn is more likely when shadows are shorter than objects are high. This is a convenient method for reducing the possibility of overexposure and sunburn especially of children in the early summer. Avoidance of long term exposure to direct sunlight when the shadow is shorter than the child can be a convenient method rather than selecting clock times. The clock times for high exposure vary with standard or daylight saving time and latitude. For darker seasons when insufficient sunlight is a common problem the midday exposure when the shadows are the shortest are preferred. At high latitudes in darker seasons even the shortest shadow in midday is longer than the person is tall.

Balancing the exposure throughout the week and year

For indoor workers, a reduction in the weekend and vacation overexposure by clothing style and avoiding the midday bright direct sunlight can help balance the exposure, reduce the exposure and reduce the risk of skin cancer.

Another approach to balancing the exposure for indoor workers is to increase the exposure during the week. Increased exposure by very short walks at lunchtime or lamp exposure may help to balance the weekday and weekend exposure. This increases the exposure and risk of non-melanoma skin cancer but for many the disadvantages may be outweighed by the advantages as discussed by Ainsley, 9. The risk of nonmelanoma skin cancer is increased, however, the reduced risk of other higher mortality conditions can reduce the overall mortality as observed for outdoor workers such as sailors.

For office workers who have a problem with too much sunlight exposure on weekends in the summer bare tube fluorescent exposure at work during the week provides an improved balance in exposure throughout the week. This increased exposure, but with a better balance throughout the week, may reduce the risk of melanoma of the skin. For persons who obtain excessive sunlight every day in the bright season, bare tube fluorescent lighting in the evening is clearly a disadvantage. For those persons blocking diffusers are appropriate during the bright season.

The lower mortality for outdoor workers indicates significant light exposure and exercise is conducive to good health for many persons.

Melanoma of the skin appears to be associated with irregular sun exposure habits and overexposure. Many sunburns are common for those who develop melanoma of the skin. In childhood too much midday summer sun with sunburns, moles and freckles can indicate an increased risk in later life. For adults and students being indoors at work or school with lots of sun exposure on weekends or vacations can increase the risk. The problem is irregular exposure. The skin is bleached and sensitive when exposed to too much sunlight.

Near the equator the melanoma of the skin incidence generally is not as high as at the bright desert environments near 30 degrees latitude. At the equator the sun is nearly vertically above at the equinoxes twice a year. In comparison at higher latitudes the sun is at a high elevation only once a year in the summer. Consequently at the equator the sunlight is bright all year with only a small percentage variation. The average irradiance during a month is high but it changes by only a small amount such as 0.22 to 0.32 watts/sq. cm., Frederick, 28. In the U.S. the irradiance varies from a high of about 0.2 watts/sq. cm. in June and July to very low values in the winter. Although the equatorial irradiance is higher the irradiance percentage change through the year is much smaller than in the U.S. and the countries with greatly increasing and high melanoma of the skin incidences.

The lower incidences of melanoma of the skin near the equator indicate the potential advantages of a balanced exposure. Usually the recommendation is to avoid sun exposure. However, to balance the exposure the exposure could be increased during the week such as a walk at lunch time and decreased on the weekend such as by avoiding midday non-shaded direct sun exposure. The objective is to obtain the benefits of sun exposure and avoid overexposure in a manner best suited for each individual with particular skin type and any special health conditions.

To balance the exposure throughtout the year the exposure can be increased in the spring and fall by opening the car windows and rolling up the sleeves and other techniques. In the higher latitudes in the winter the solar irradiance is so low lamps are about the only way to obtain significant exposure. For daily moderate exposure lamps at home or work can be used to maintain sufficient skin exposure.

Tanning booths have the disadvantage they are usually used for high intensity irregular exposures to provide an excessively dark stressful tan with associated skin damage. Frequent moderate exposures with light or no tanning is much less stressful for the skin. Since outdoor workers generally have a lower mortality than indoor workers exercise and light exposure with moderate tanning may be of benefit to many persons.

Avoidance of overexposure by high sensitivity individuals

The exposures such as 0.02 MED for whole body vitamin D generation are very low compared to casual summer exposure. Even though the exposure is low, precautions as used with ultraviolet therapy may be advisable since some persons may be very sensitive to the ultraviolet radiation. For some individuals with increased sensitivity to UV-B radiation the avoidance of excess ultraviolet exposure may be essential. Xeroderma pigmentosum, sarcoidosis, Bell, 15, and other conditions require special care in controlling any UV-B exposure.

As discussed by Scott, 69: "There are certain skin conditions in which the application of ultraviolet radiation may lead to an exacerbation. These include the acute onset of psoriasis, acute eczema, lupus erythematosus, herpes simplex, and xeroderma pigmentosum. There are also some general conditions in which irradiation should be used with caution. Among these are pulmonary tuberculosis, cardiac or renal failure, hyperthyroidism, and diabetes. Nervous, cachetic patients do not tolerate irradiation well. The administration of sulphonamide preparations sometimes leads to prolonged and persistent sensitivity."

"Extensive treatments at home by the patient is to be avoided without the supervision of a physician. Home lamps should be fitted with an automatic switch to prevent overdosage in case the patient should inadvertently fall asleep. Kovacs, has shown that there are many electrical and mechanical dangers in carrying out home treatments."

Scott, 69, also points out whoever may face the source should wear eye protection and the genitalia are usually covered during irradiation. (Beneficial effects of genitalia exposure during sunbathing such as hormone production and softening the skin for childbirth are discussed by Kime, 42.) A three week progressive increase in exposure starting with a short exposure of the feet working up to a whole body exposure is described on page 257 of the article by Scott. The many chemicals and drugs that can photosensitize the skin and eyes make it desirable to gradually increase any new exposure.

The appearance of skin disorders, itching or other unusual conditions indicate the exposure should not be continued and a physician consulted. Photosensitization materials include drugs (quinine, trypaflavin, eosin, methylene blue, and other fluorescent dyes), endrocrines (insulin, adrenalin, pituitrin, thyroid) and heavy metals (mercury, iron, bismuth, gold, silver and calcium and their salts), Kovacs, 44.

Hawk, 37, describes idiopathic abnormal responses to ultraviolet radiation including the most common photodermatosis, polymorphic (or polymorphous) light eruption (PLE). PLE is more common in females than males and usually caused by sunlight and not by high doses of artificial light. The skin eruption usually begins in the spring. Hawk lists twenty one diseases exacerbated by excess ultraviolet radiation: acne, actinic foliculitis, atropic eczema, carcinoid syndrome, cutaneous T-cell lymphoma, dermatomyositis, disseminated superficial actinic porokeratosis (DSAP), erythema multiforme, familial benign chronic pemphigus (Hailey—Hailey disease), keratosis follicularis (Darier's disease), lichen planus, lupus erythematosus (LE), pellagra, pemphigus foliaceus (erythematosus), pityriasis rubra pilaris, psoriasis, reticulate erythematous mucinosis (REM) syndrome, rosacea, seborrheic eczema, transient acantholytic dermatosis (Grover's disease), and viral infection. For persons with these disorders, physician consultation and the avoidance of excess ultraviolet exposure is of increased importance.

Harber, 35, describes abnormal responses to ultraviolet radiation resulting from drugs and chemicals. Phototoxic chemicals include dyes, coal tar derivatives and furocoumarins. Photoxic drugs include: amiodarone, benoxaprofen, demethylchlortetracycline, doxycycline, furosemide, nalidixic acid, naproxen, phenothiazines, piroxicam and sulfonamides. He also lists major photoallergenic drugs and chemicals including particular halogenated salicylanilides, antifungal drugs, phenothiazines, suncreens, whiteners, fragrances and sulfanilamides. Photoxic reactions normally occur within 24 hours. Photoallergenic reactions may not appear for periods such as 10 days later. For persons with these types of photosensitive reactions physician consultation and avoidance of excess ultraviolet exposure is of importance.

Light skin persons living in bright climates have high sensitivity to sunlight relative to those with darker skin better adapted for the local climate. In the U.S. light skin persons living in southern bright climates typically have problems with summer overexposure. Dark skin persons living in the northern darker climate typically have greater problems with winter underexposure. The average 25-OHD blood level in Palm Beach is approximately 80 ng/ml, Neer, 58, and even higher values are expected in the summer and for outdoor workers.

Those living in bright climates in high elevation areas are exposed to very high levels of UV-B. The shorter path through the atmosphere results in less atmospheric absorption and scattering of the UV-B solar radiation. The avoidance of bright season overexposure in the high elevation areas thus can be important, especially for light skin persons. The benefit of the relatively high exposure in other seasons may offset the disadvantage of the high summer exposure. Scragg in his chapter 9 in the 1995 CRC book Calcium-Regulating Hormones and Cardiovascular Function edited by M. Crass III and L. V. Avioli points out that both coronary heart disease (CHD) mortality and elevation vary with longitude in the United States (but in opposite directions). High elevation areas in the west have much lower CHD mortalities than lower areas in the east. Scragg concluded the increased ultraviolet radiation at higher elevations is the most likely factor explaining the longitudinal variation of CHD mortality.

The malignancy mortality also varies in a manner similar to the variation of CHD with longitude. Increased ultraviolet radiation especially in the dark seasons thus may reduce the mortality from malignancies. Multiple sclerosis varies relatively uniformly with latitude across the United States. The longitudinal variation in the United States characteristic of CHD and malignancy mortalities is not apparent for MS. Visible light, temperature or some other factor may influence the risk of multiple sclerosis. UV-B (if it is a risk factor) is not likely to be as strong a risk factor for multiple sclerosis as other factors.

Vieth, 79, discusses a possible mechanism for vitamin D toxicity. High levels of plasma 25-OHD may displace 1,25 dihydroxyvitaminD from the plasma. Excess vitamin D symptoms are similar to vitamin D deficiency symptoms as discussed in the U.S. Department of Health and human Services publication 88-2117 on Some Facts and Myths of Vitamins. In southern states solar radiation stimulated levels of 25-OHD are high for many individuals. For persons with very high levels of 25-OHD due to dietary intake of vitamin D and sun exposure the use of additional lamp induced vitamin D thus may be detrimental and should be avoided.

By using low irradiance lamps for low daily whole body exposures in northern areas in the dark seasons and avoiding excess exposure in bright seasons the risks of home use are greatly reduced. The exposures for whole body stimulation of vitamin D formation in the skin are in general much lower than the exposures used for treatment of skin disorders. By observing the precautions developed for skin disorder treatment such as using timers in case the person being exposed falls asleep, the safety of exposure is increased. Physician consultation is needed for selecting exposure conditions for those persons who have abnormal photosensitive reactions.

Summary

For good health, exposure to a variety of wavelengths is needed. A balance in the exposure from day to day and throughout the year is necessary. Avoidance of overexposure by having moderation in the exposure is essential to prevent skin cancer and other disorders. Excess vitamin D in the diet should be avoided. The diet should be balanced including sufficient fruits, vegetables and antioxidants. A bright environment is desirable for a feeling of well being and avoiding psychological depression.

The present invention can enhance the probability for good health and reduce the risk of diseases associated with solar radiation exposure and diet for those persons with deficient, excess or non-balanced exposure and diet. A key feature of the invention is the use of whole body exposure when possible. This enables the use of very low irradiances for short periods. A slight reduction in the bright season exposure can then more than offset the increased dark season exposure. This results in an overall reduction in the risk of skin cancer. Several techniques are included to increase the UV-B exposure in cold dark seasons when a deficiency in UV-B exposure is common.

BRIEF DESCRIPTION OF THE DRAWINGS

For a fuller understanding of the nature and objects of the invention, reference should be had to the following detailed description taken in connection with accompanying drawing forming a part of this specification and in which similar numerals of reference indicate corresponding parts in all the figures of the drawing.

FIG. 13 is a schematic view of an embodiment of a lamp fixture with adjustable ultraviolet output.

FIG. 14 is a sectional view taken along line 14—14 of FIG. 13.

FIG. 15 is a schematic view of the FIG. 13 lamp fixture adjusted for minimum ultraviolet radiation output.

DESCRIPTION OF THE PREFERRED EMBODIMENTS

The above and other objects and advantages and novel features of the present invention will become apparent from the following detailed description of the preferred embodiment of the invention illustrated in the accompanied drawings, wherein:

Adjustable ultraviolet transmission window

Figure 6:
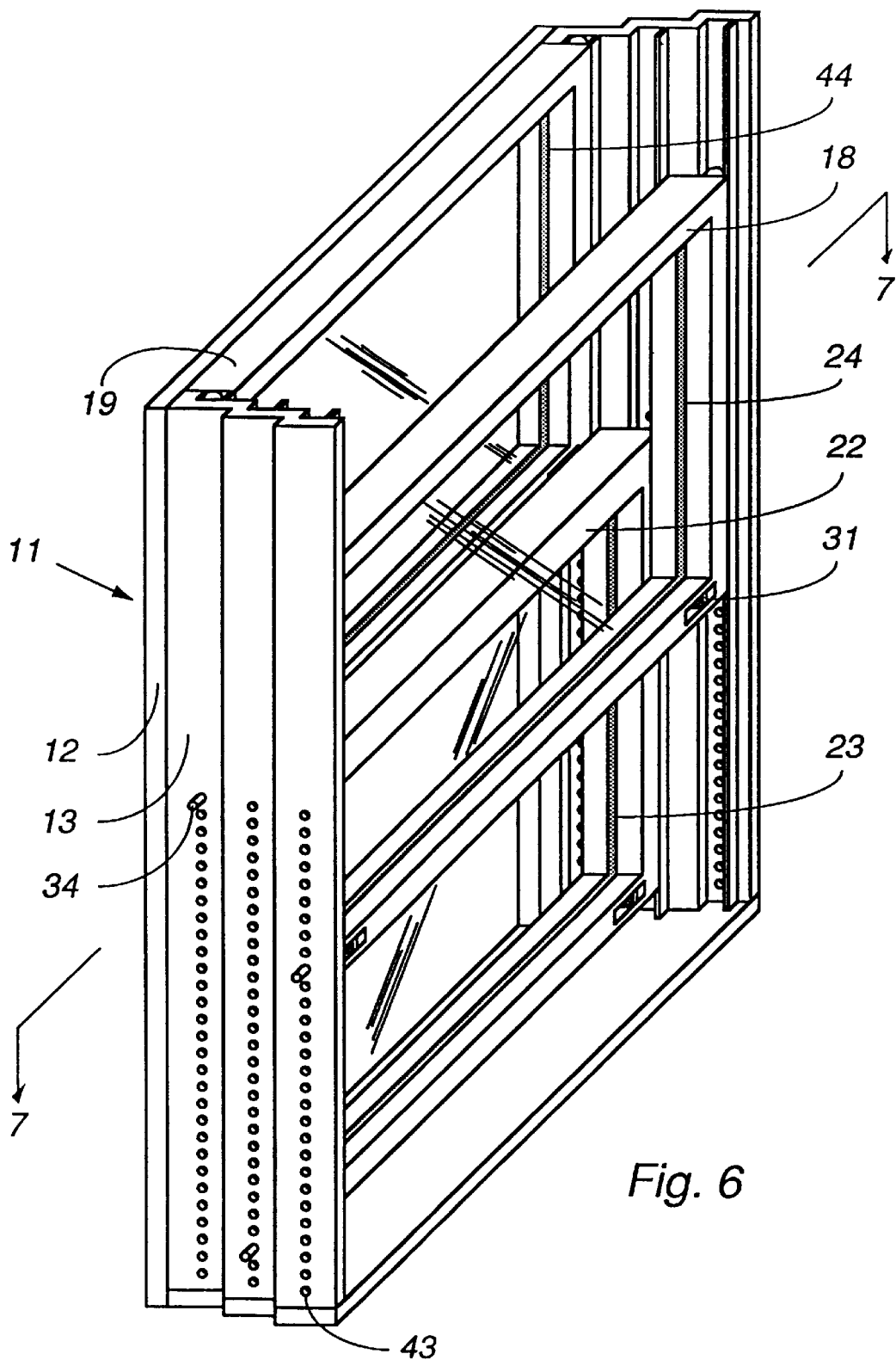
FIG. 6 is an oblique view of an embodiment of the window assembly of the present invention.
Figure 7:
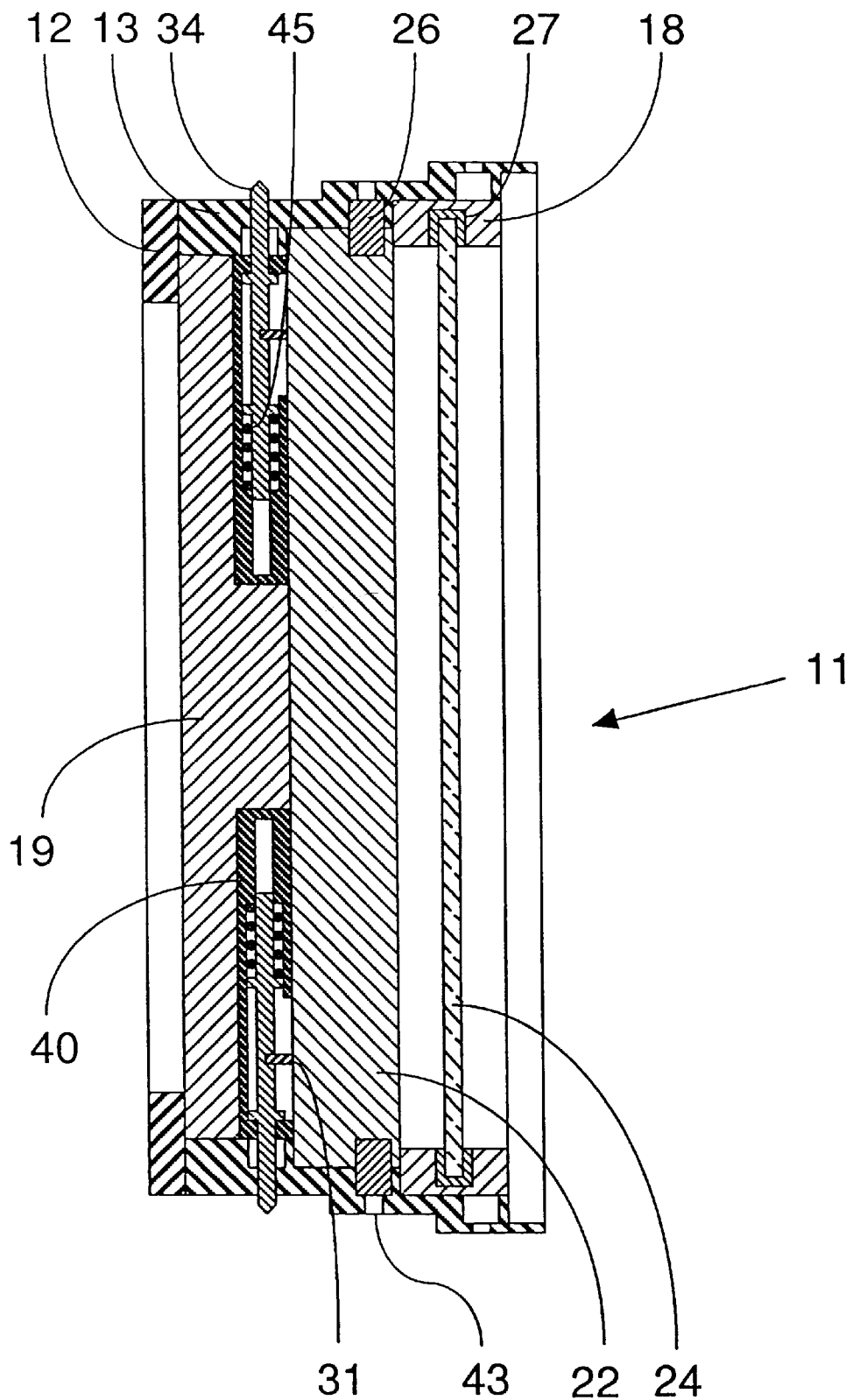
FIG. 7 is an enlarged horizontal sectional view taken along line 7—7 of FIG. 6.

FIG. 6 is an adjustable window, 11, of know construction which is currently available. The sections are positioned for intermediate ultraviolet transmission;

Referring now to the sectional view in FIG. 7, the outer frame, 12, along with the side supports, 13, are used to support the movable windows 19, 22, and 18. The ultraviolet transmitting window is the outer window, 19. The windows in the middle, 22, and inner, 18, units block the ultraviolet UV-B (280–315 nm) radiation.

A window insert, 24, is held by a grommet, 27. The window is guided along the track by the guide, 26. The retractable pins, 34, enable the window to be positioned manually using the handles, 31. The pins are held engaged in positioning holes, 43, by the springs, 45, located in holders 40.

Referring now to FIG. 6, for maximum ultraviolet transmission, the inner window, 18, is lowered so the outer ultraviolet transmitting window, 19, is unobscured. For maximum blocking of the ultraviolet radiation the inner window, 18, is raised to the top to block the ultraviolet radiation passing through the outer window, 19. For intermediate ultraviolet transmission, the inner window, 18, is positioned at an intermediate position as illustrated in FIG. 6.

The UV transmitting window, 19, has an insert, 44, composed of material that is substantially transparent to light rays from the ultraviolet, visible, and part of the infrared solar spectrum. The UV blocking sections, 18, and 22, are substantially transparent to the visible and infrared solar radiation. The side frames, 13, hold the windows and allows them to be positioned for high, intermediate or very low ultraviolet radiation transmission.

To raise or lower a window the two positioning pin handles, 31, are moved toward each other by actuator means to release the pins from the positioning holes freeing the window. The window is then moved up or down by actuators and the pins are released when the window is in the desired position. When the pins engage the holes the window is held in place and the actuators can be released.

The material of which the ultraviolet transmitting window, 19, insert, 44, is composed is an optically transmitting material such as ultraviolet transmitting glass or plastic similar to the materials described by Driscoll, 23, and by Sliney, 73, hereby incorporated into the present application by this reference. Briefly the materials are glasses such as Pyrex, trademark, that transmit a fraction of the ultraviolet B radiation and are not extremely high in cost. Other glasses such as Vycor, trademark and fused silica transmit a higher fraction of the ultraviolet radiation but the cost is prohibitive for many applications. Plastic materials such as Corex-D, trademark, and Plexiglas, trademark, have high transmission in the UV-B. However, many of the plastic materials are not solar resistant and darken upon long term exposure to sunlight and are satisfactory only for low exposure.

The material of which the ultraviolet B radiation blocking inserts, 23 and 24, are composed is conventional window glass or plastic.

The general UV-B non-direct solar radiation environment in a room is increased when the UV-B transmitting area is increased. In any area with direct solar irradiation through a specularly transparent window the area irradiated by UV-B is increased when the UV-B transmitting area is increased. The direct irradiation is not altered. The risk of overexposure is reduced by use of a diffusely UV-B transmitting window 19, insert, 44, of the preferred embodiment.

A meter can be used to measure the ultraviolet solar radiation transmitted by the window. Estimates of the appropriate exposure for a person with paticular skin type is needed to determine the exposure time for window transmitted or lamp generated ultraviolet B radiation.

Adjustable ultraviolet transmission sunroof

Figure 1:
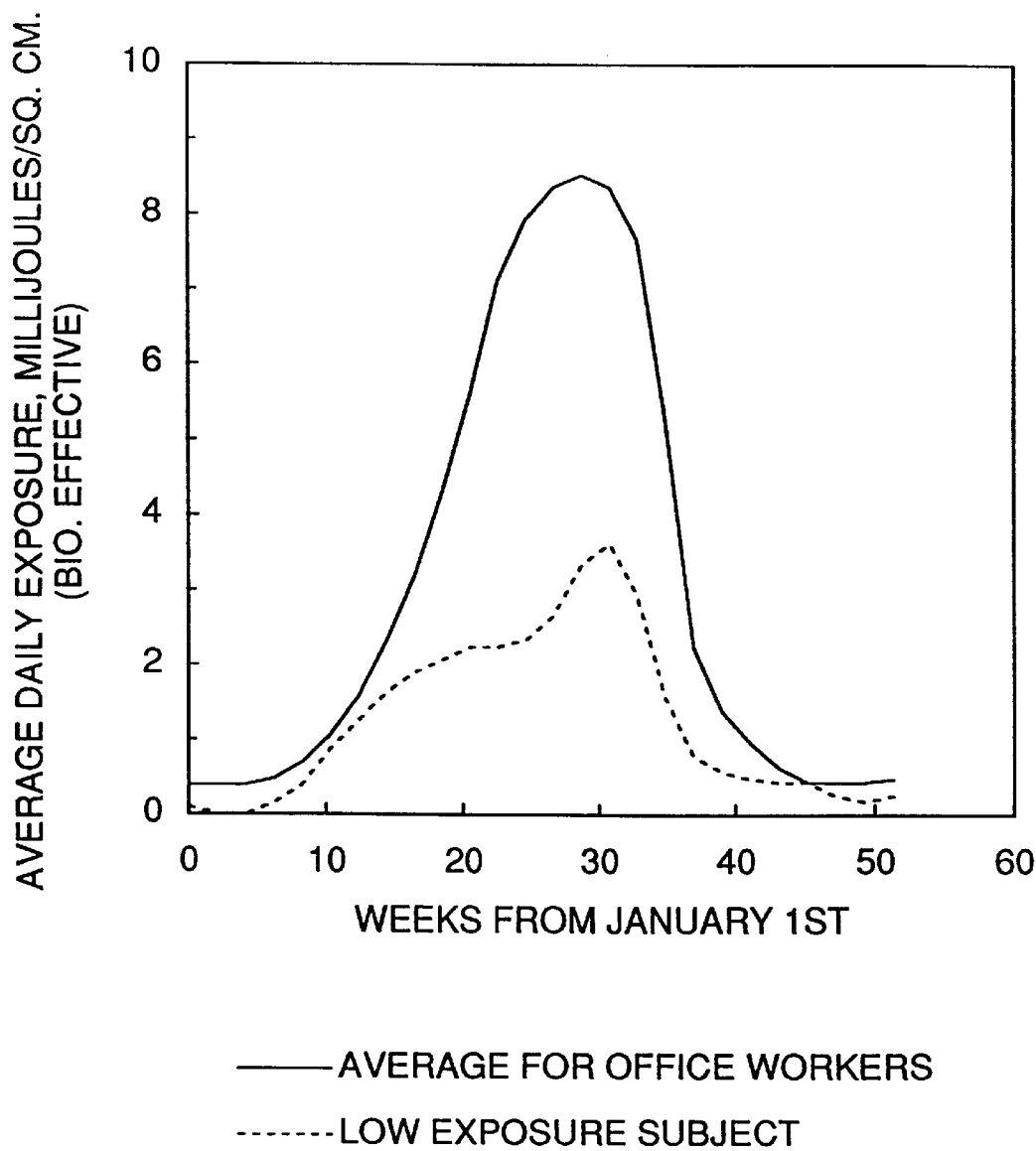
FIG. 1 is a graph of the average daily sunlight exposure over the course of the year.
Figure 2:
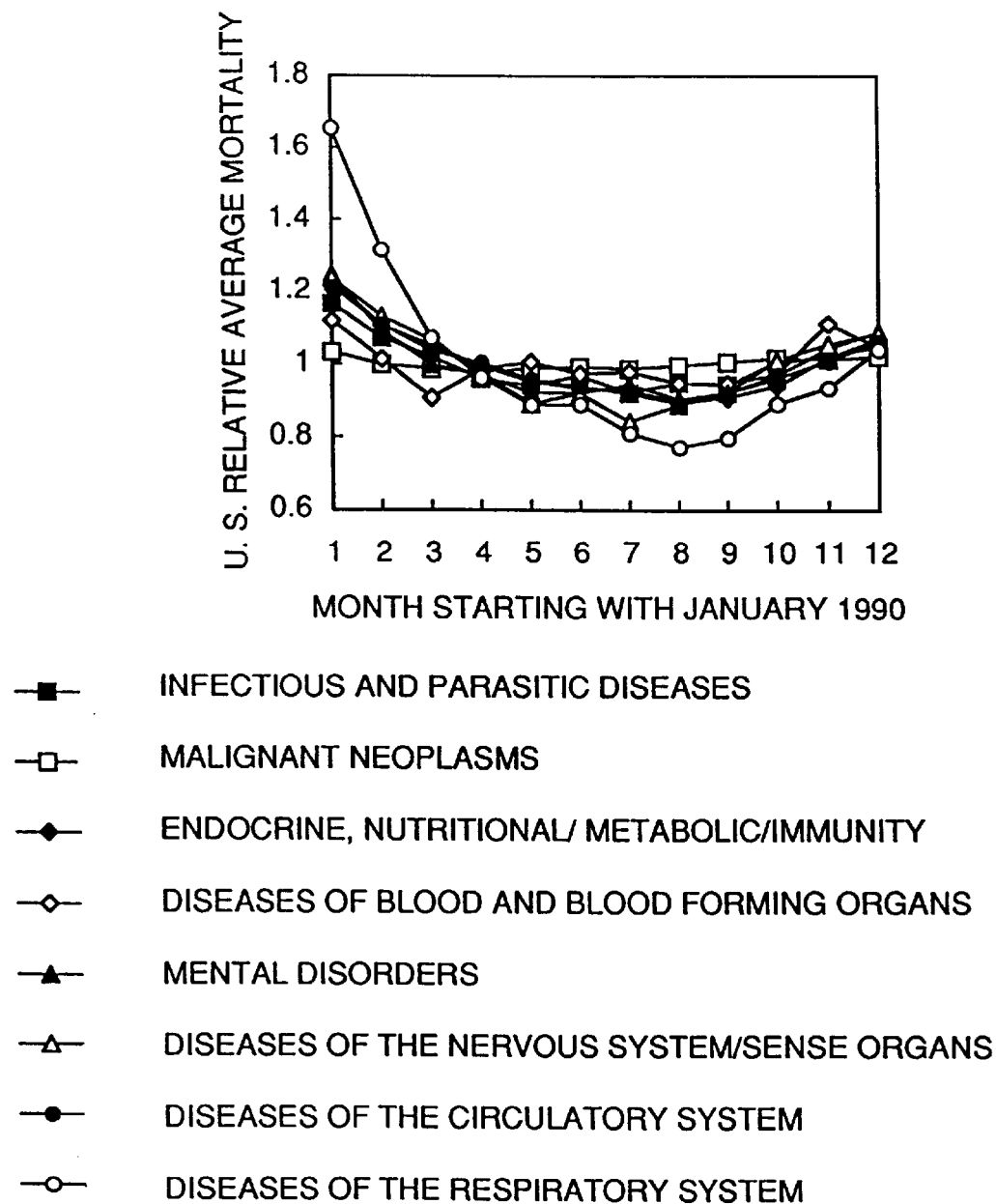
FIG. 2 is a graph of the U.S. mortality rate for the year 1990.
Figure 3:
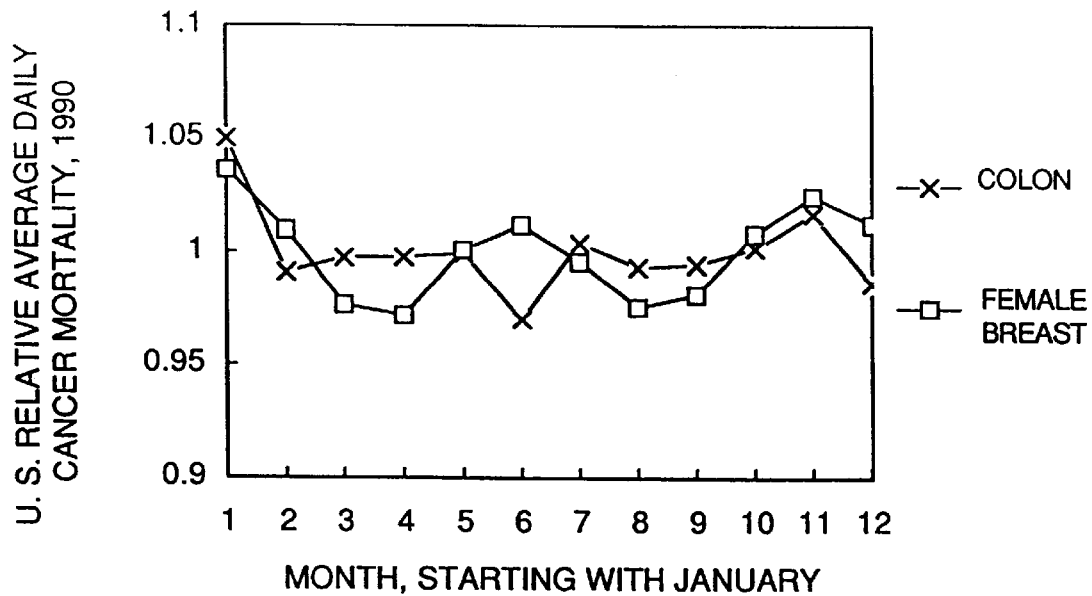
FIG. 3a and FIG. 3b are graphs of the U.S. breast and colon cancer mortality rates for 1989 and 1990.
Figure 3:
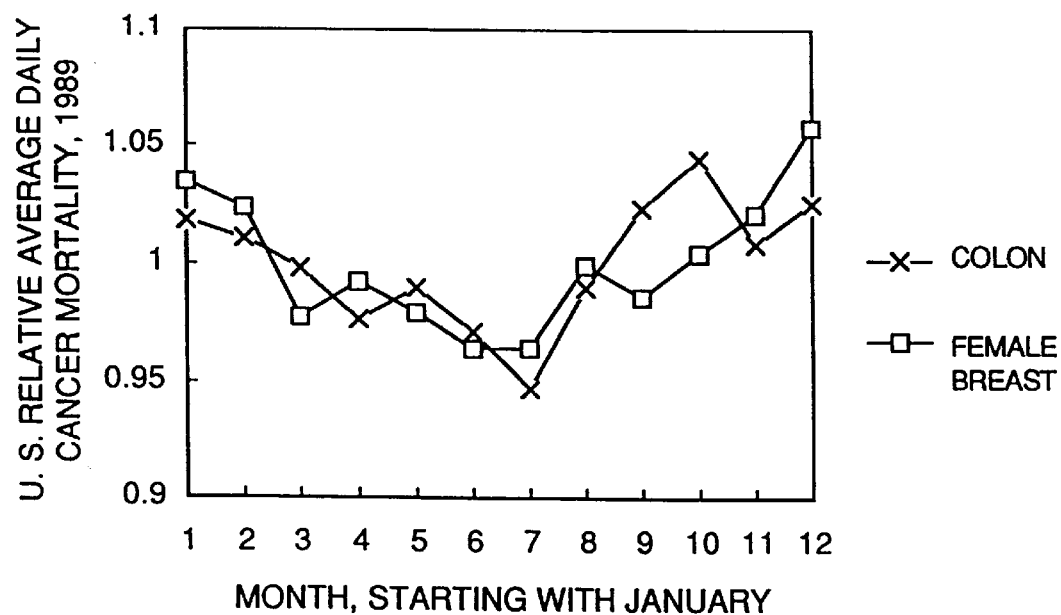
Figure 4:
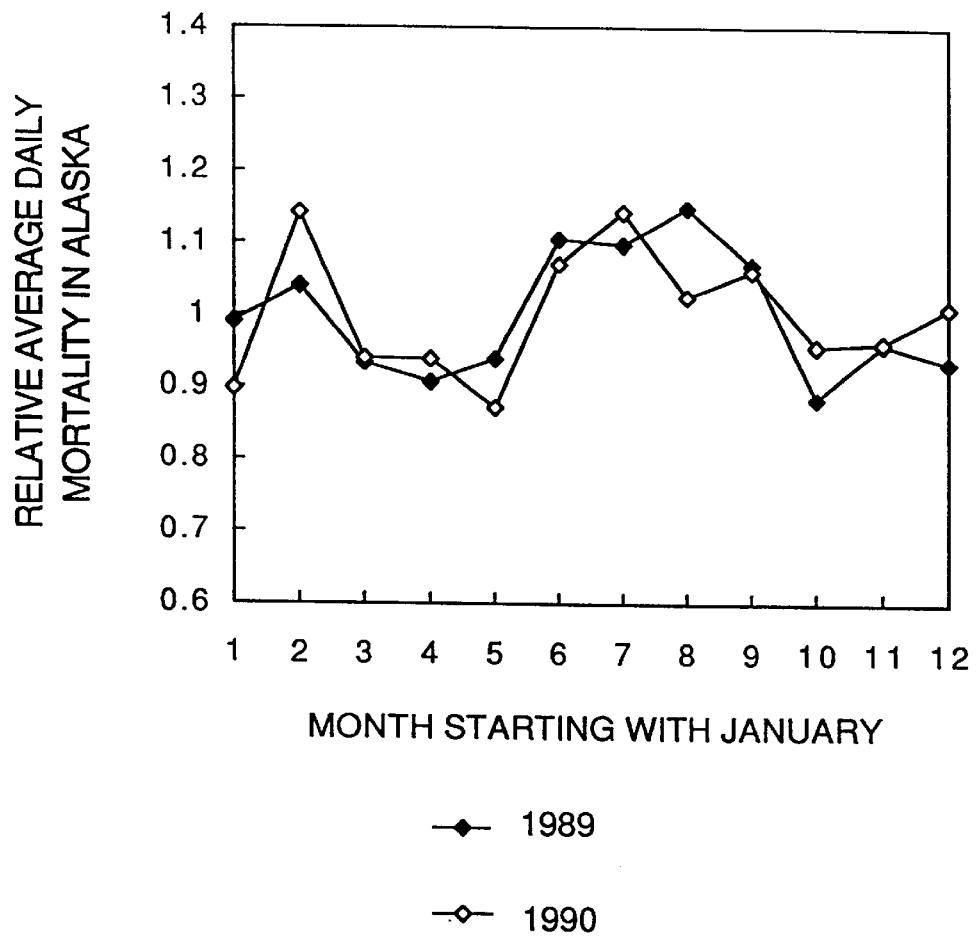
FIG. 4 is a graph of the Alaska mortality rate for 14989 and 1990.
Figure 5:
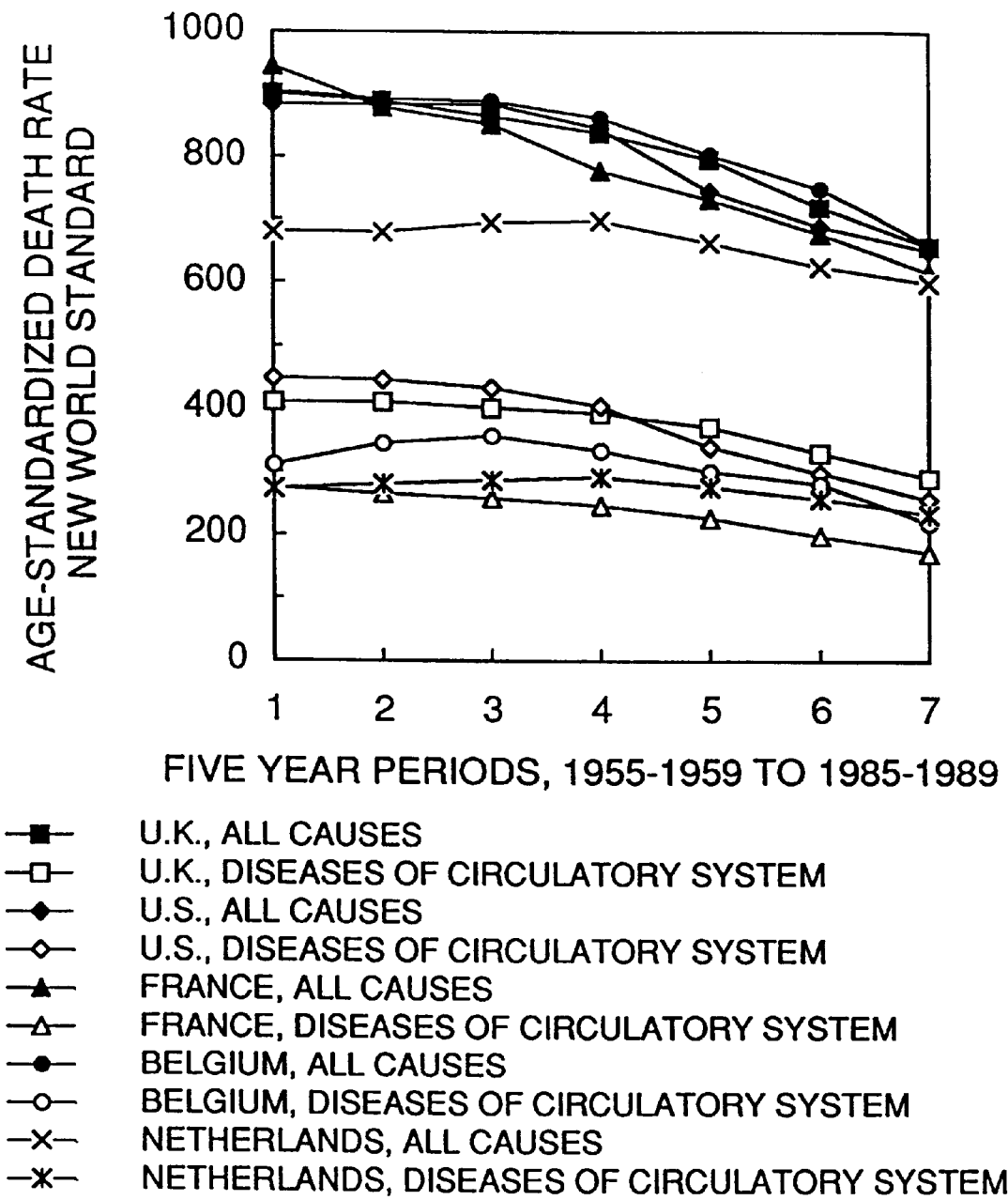
FIG. 5 is a graph of various countries' mortality rates over 5 year periods from 1955 through 1989.
Figure 8:
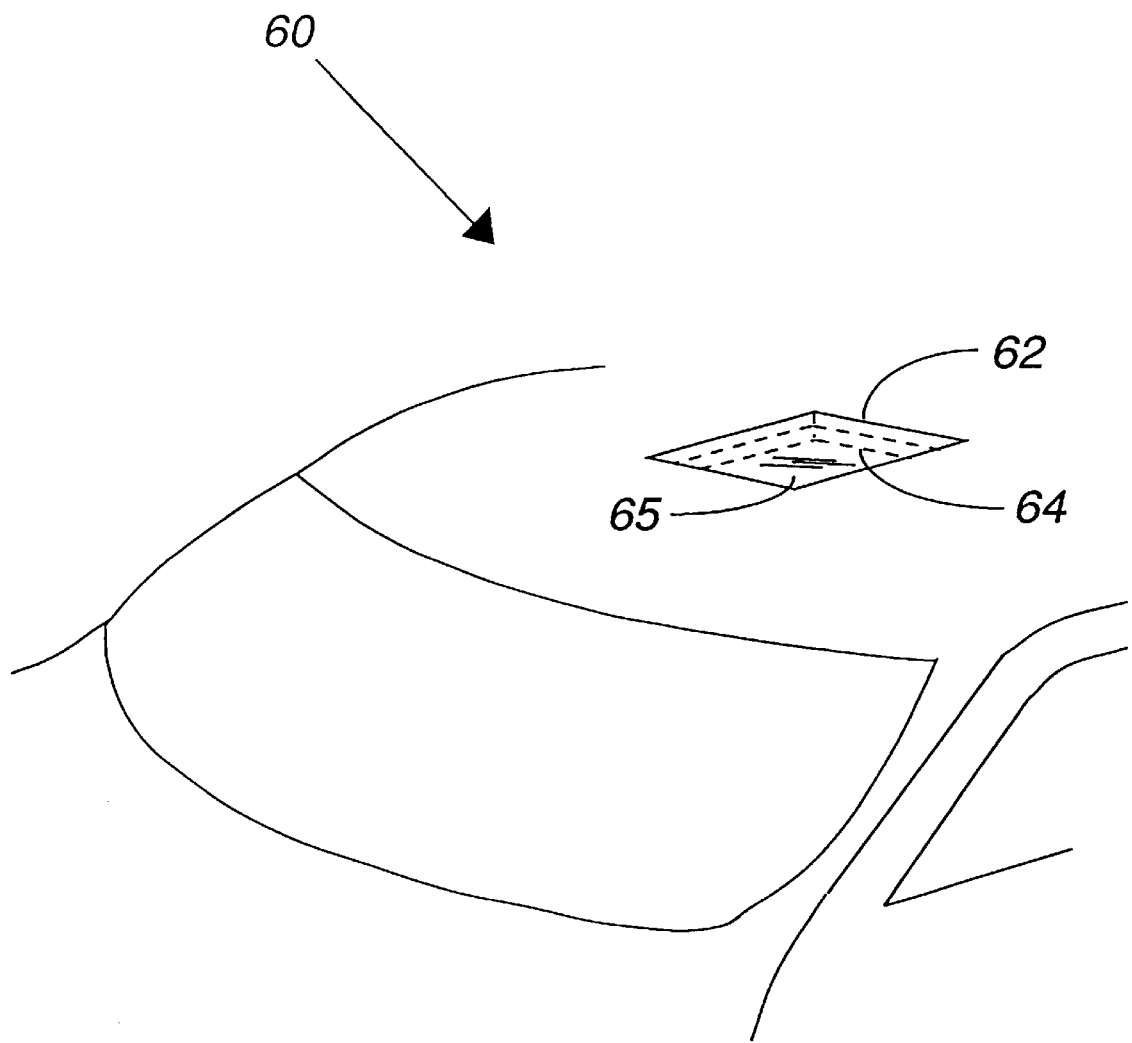
FIG. 8 is a schematic view of an embodiment of the vehicle sun roof of this invention.

FIG. 8 is an adjustable ultraviolet transmission sunroof, 65, for a vehicle, 60. The outer element, 62, is ultraviolet diffusely transmitting material. The inner sliding element, 64, blocks the ultraviolet radiation and attenuates the visible light. By positioning the inner sliding element, 64, the ultraviolet transmission can be adjusted. The method of operation is similar to the window in FIG. 1. The inner section, 64, is partially transparent to visible light to avoid glaringly bright light transmission when the sun is overhead.

A person receiving too little or too much ultraviolet B radiation can adjust the sunroof, 65, for appropriate UV-B transmission. A person receiving sufficient UV-B radiation while outside the vehicle can position the sliding element, 64, to block the ultraviolet B radiation.

Ultraviolet radiation transmitting garment

Figure 9:
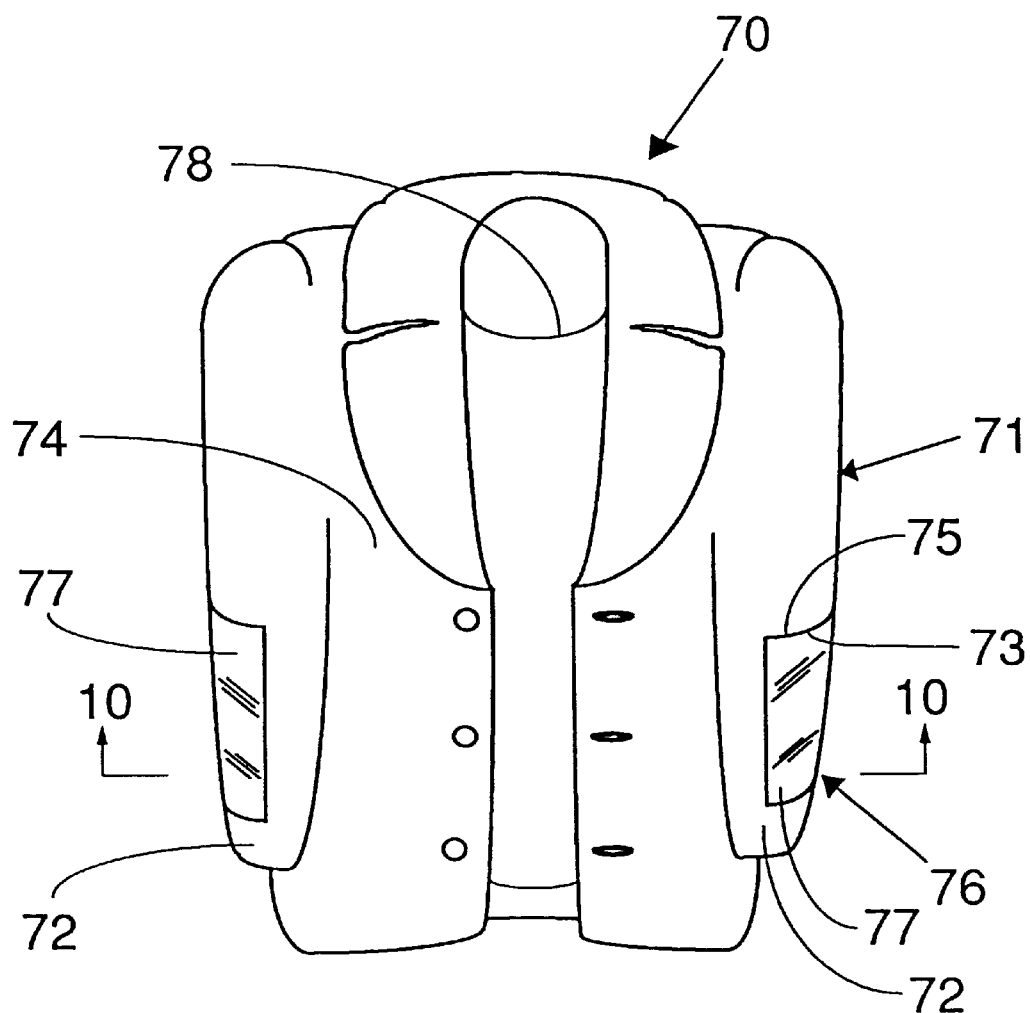
FIG. 9 is a schematic view of an embodiment of a garment with transmitting windows.

FIG. 9 is a garment, 70, with a first body portion, 74, with a second portion 71 including sleeves 72, with the second portion including a third portion 76, including windows, 77. The windows, 77, are composed of material that is substantially transparent to light rays from the ultraviolet, visible, and infrared solar spectrum and in particular UV-B radiation. The material of which the windows, 77, are composed is an optically transmitting material such as plastic, safety glass or woven fabric of plastic or glass fibers. The window, 77, can be attached to the garment, 70, using thread, 75, and stitching holes, 73, in the edges of the window. For some materials such as thin flexible plastic the stitching holes, 73, are not necessary as the window can be machine sewn to the garment, 70. A long sleeve shirt, 78, can be worn under the coat to avoid overexposure during midday in bright cold environments such as in high altitude areas. The sleeves can be rolled down in midday for protection. In the morning and late afternoon the sleeves can be rolled up to provide UV-B exposure of the skin as needed.

Figure 10:
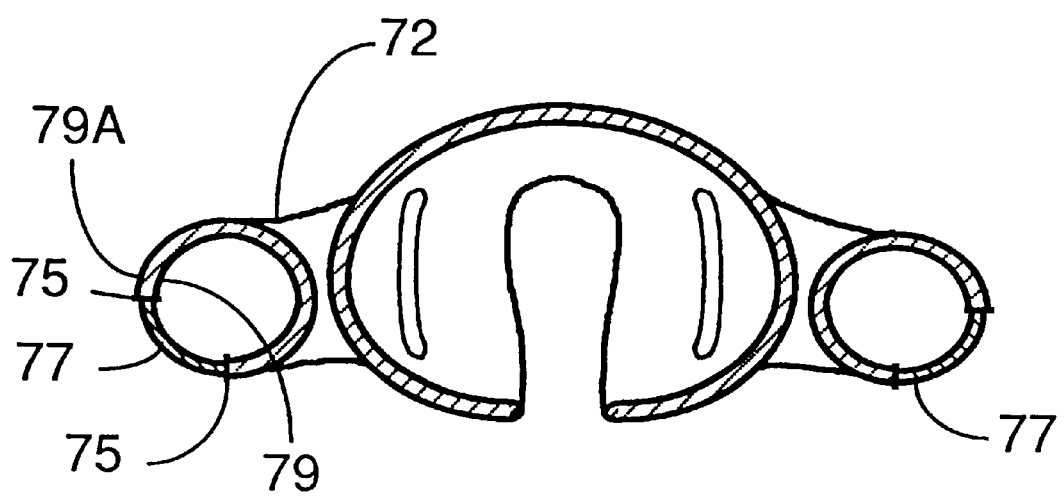
FIG. 10 is an enlarged horizontal sectional view taken along line 10—10 of FIG. 9.

FIG. 10 is a sectional view of the garment, 70, taken along line 10—10 of FIG. 9. The windows, 77, in the sleeves, 7, are attached by stitches 75, to the inner fabric layer 79, and the outer fabric layer 79A.

Garment for protecting the skin from excessive solar radiation exposure

Figure 11:
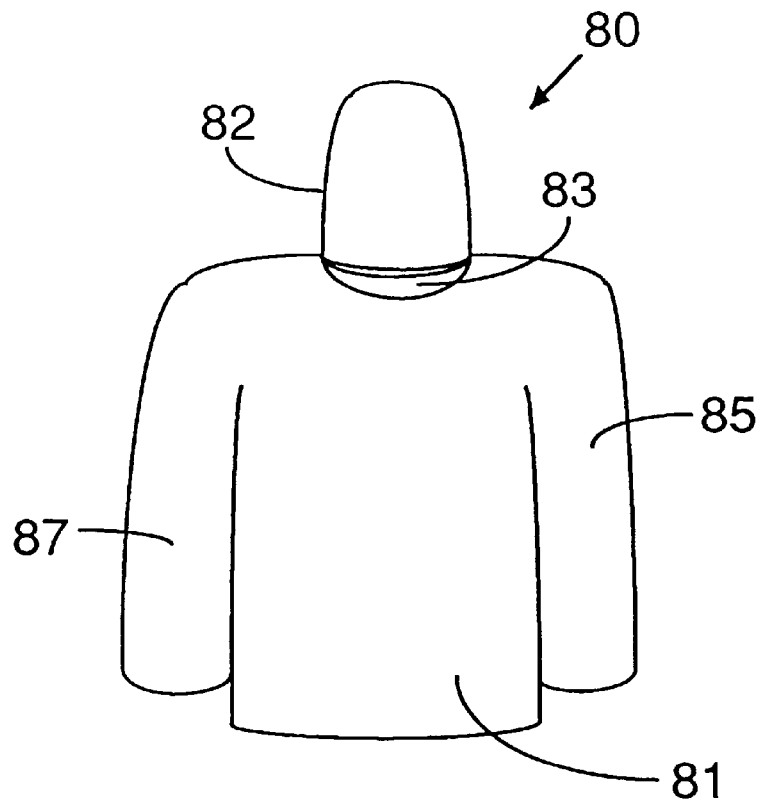
FIG. 11 is a schematic back view of an embodiment of a protective garment

FIG. 11 is a garment, 80, for protecting the skin from overexposure including body portion, 81, and arms, 85, 87.

Figure 12:
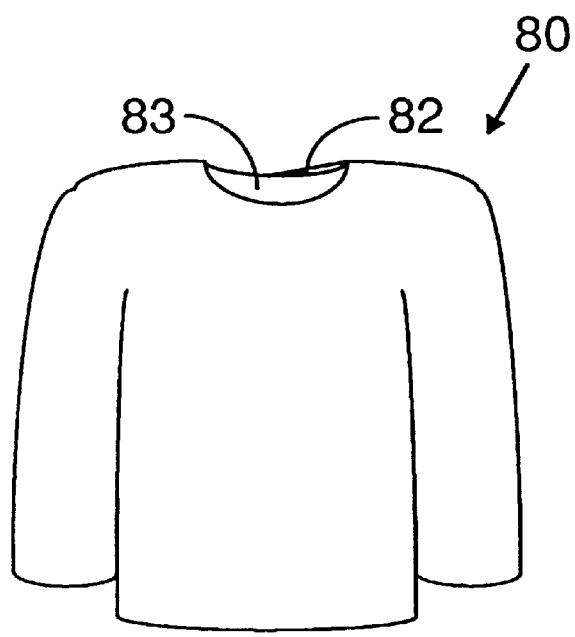
FIG. 12 is a schematic back view of the protective garment of FIG. 11 with the hood stowed in the hood pocket.

A hood 82, can be used to shade the head and neck. A novel feature is the pocket 83, for stowing the hood when it is not in use. FIG. 12 shows the garment, 80, with the hood, 82, stowed in the pocket 83.

The loose fitting garment body portion, 81, allows ventilation for cooling by removal of humid air near the skin during hot weather. The material of which the garment, 80, is composed is a fabric, 84, such as white woven cotton strands. This material provides transmission of a very small fraction of the solar radiation suitable for exposure of the skin. The white color provides reflection of a large fraction of the solar radiation for maintaining coolness in a hot environment. This material for a loose fitting garment permits ventilation and allows moisture transmission and or absorption for cooling of the wearer by evaporation of moisture from the skin.

Referring now to FIG. 11, when a person is wearing the garment, 80, indoors or elsewhere where the hood, 82, to shade the head from sunlight is not needed, the hood 82, can be stowed in the pocket 83, as shown in FIG. 12.

Adjustable ultraviolet radiation output light fixture

FIG. 13 is a light fixture, 90, having side walls, 91, and end walls, 94, for providing adjustable UV-B radiation and light in an indoor environment. It is particularly well suited for use in a bathroom to provide whole body exposure during bathing. The UV-B radiation is emitted from fluorescent lamps, 95. Stationary UV-B blocking diffusers, 96, are located at the ends of the fixture, 94. UV-B blocking movable diffusers 97 can be used to adjust the amount of UV-B radiation emitted by the unit.

FIG. 14 is a sectional view of the light fixture, 90, along line 14—14 of FIG. 13. Referring now to FIG. 14 the two fluorescent lamps, 95, emit the visible, infrared and ultraviolet radiation. The portion of the radiation striking the diffusers, 96 and 97, is partially diffused and partially absorbed. The material for the diffusers, 96 and 97, is selected so that most of the visible radiation is diffused and most of the UV-B radiation is absorbed. This is a characteristic of most currently used diffuser materials.

FIG. 15 is an oblique view of the light fixture, 90, with the movable diffuser sections 97, positioned to block the UV-B radiation. Positioning of the movable diffusers 97, between the full open position shown in FIG. 13 and the full closed position shown in FIG. 15 provides intermediate levels of the UV-B radiation environment.

By mounting the fixture 94, facing upward on a wall, rather than on a ceiling facing downward, a more uniform indirect irradiation can be provided. In addition to providing a By mounting the fixture 94, facing upward on a wall, rather than on a ceiling facing downward, a more uniform indirect irradiation can be provided. In addition to providing a more uniform UV-B radiation environment, the visible light environment is more comfortable for the eyes without bright ceiling sources of light. This is especially important for a reclining person in some situations such as in a hospital bed. A UV-B meter, not shown, can be used to adjust the movable diffusers, 97, to provide the desired UV-B environment. For indirect UV-B lighting special ceiling materials are necessary. Most materials other than metals have very low UV-B reflectance.

Skylight with adjustable ultraviolet radiation transmission

Figure 16:
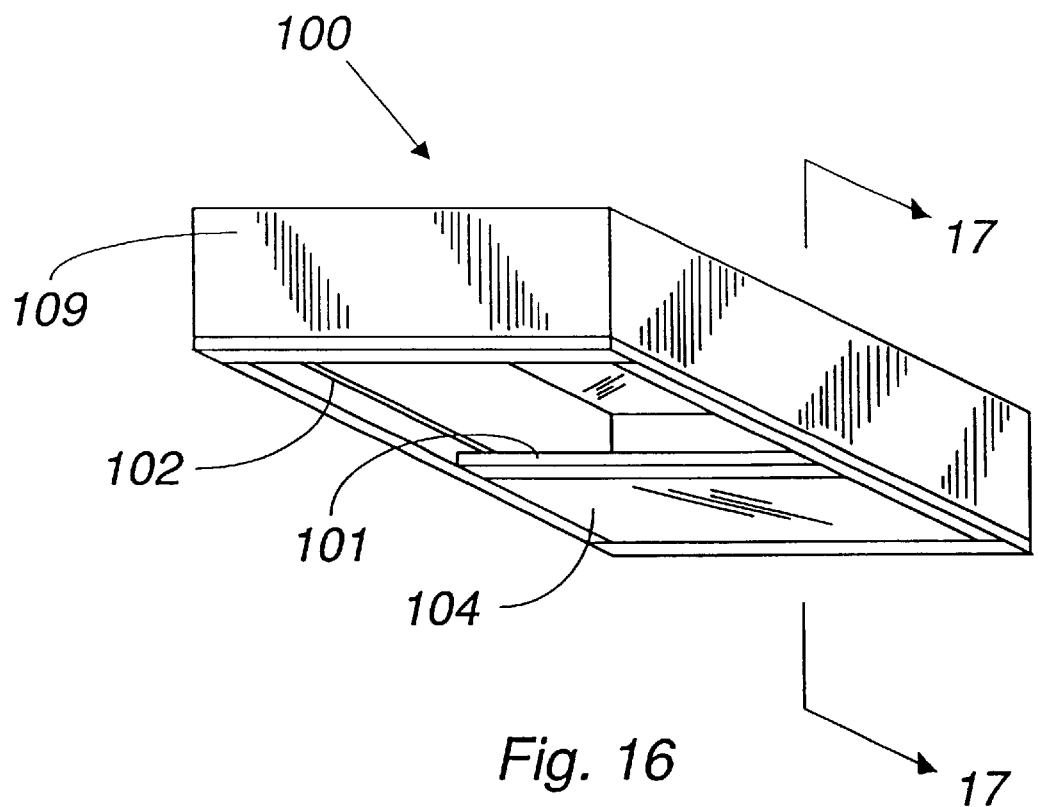
FIG. 16 is a schematic view of an embodiment of a skylight with adjustable ultraviolet radiation transmission controlled by a motor drive.

FIG. 16 is a skylight, 100, having body portion, 109, and lead screw, 102, for positioning of the UV-B blocking element, 101. A stationary UV-B blocking element, 104, is located at one end of the skylight.

Figure 17:
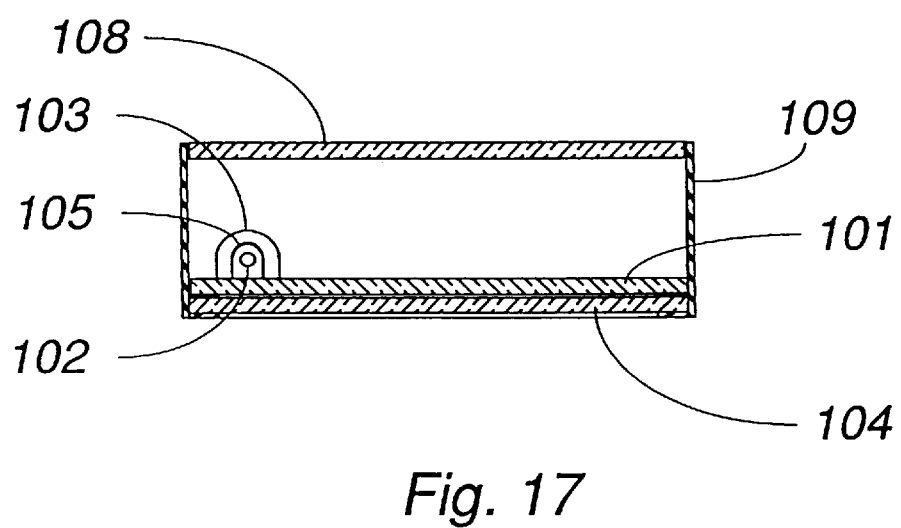
FIG. 17 is a sectional view taken along line 17—17 of FIG. 16.

FIG. 17 is a sectional view along line 17—17 in FIG. 16. A rider, 105, on the lead screw, 102, is attached to the movable UV-B blocking element, 101. The stationary blocking element, 104, is located near and parallel to the movable element, 101, as shown in FIG. 16. The drive motor, 103, can be remotely controlled to position the movable element to increase or decrease the area transmitting UV-B radiation. The outer element, 108, diffusely transmits ultraviolet, visible and part of the infrared solar radiation. The outer element also serves as a weather shield for rain, snow, sleet and wind.

Combined fluorescent and incandescent light fixture

Figure 18:
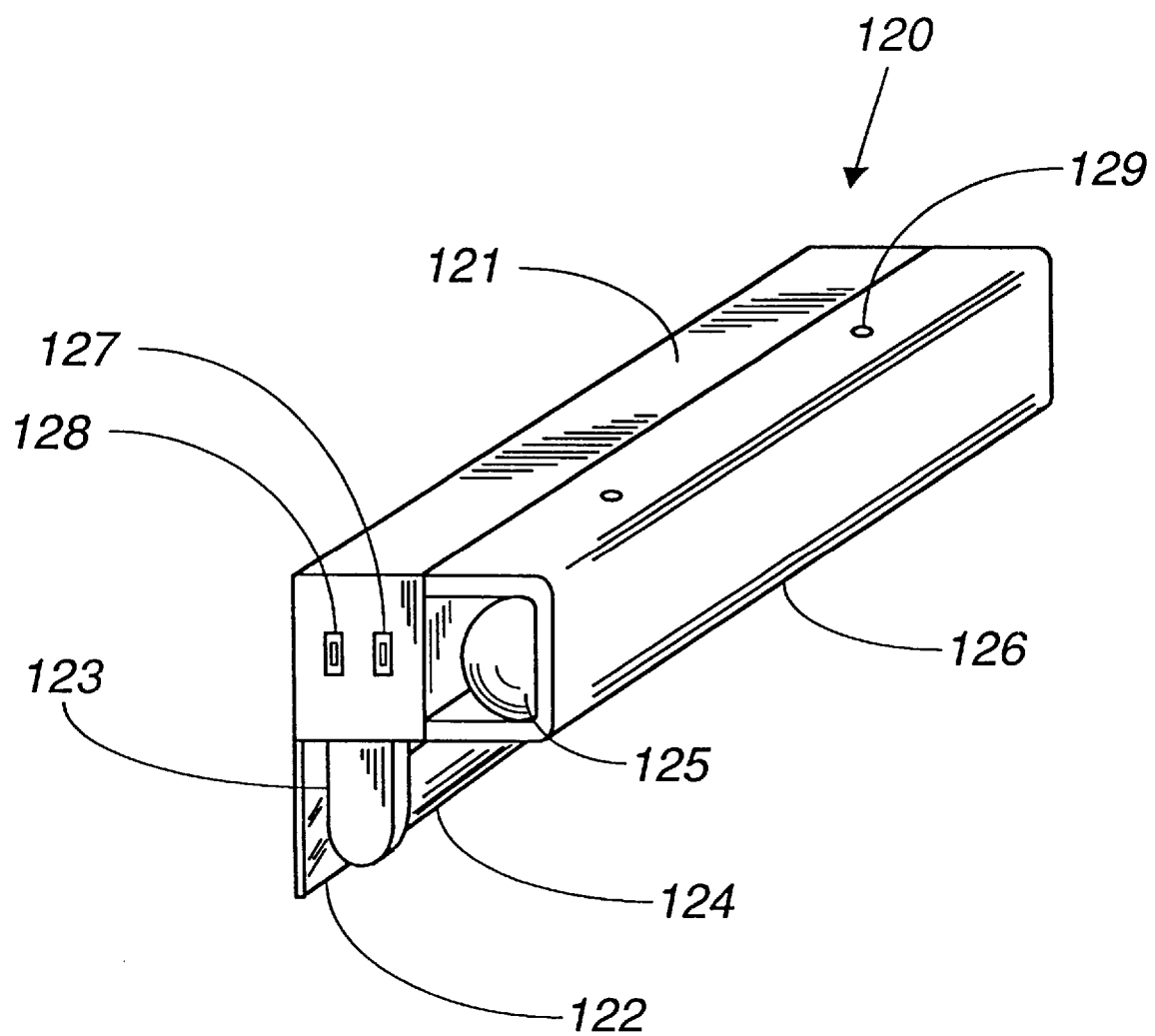
FIG. 18 is a schematic perspective view of a combined fluorescent and incandescent lamp fixture.

FIG. 18 shows an embodiment of the combined fluorescent and incandescent lamp fixture. The fixture is primarily for use in a bath room over a mirror, however, it can be used over a kitchen sink or other location. The fluorescent lamp can be used in the dark winter months to obtain ultraviolet skin exposure for formation of vitamin D. In the other months when sufficient or excess skin exposure is obtained from casual sun exposure the incandescent lamps can be used. The use of the incandescent lamps with very low ultraviolet radiation output during periods of sufficient sun exposure reduces the risk of skin cancer and other diseases associated with ultraviolet radiation overexposure.

The fixture, 120, includes a fixture mounting box, 121, to which is attached a reflective plate, 122. A fluorescent lamp holder ependsfrom and is integral with box, 121. lamp switch, 127, controls the incandescent lamps, 125, and a fluorescent lamp switch, 128, controls the fluorescent lamp, 124.

The switches 127 and 128 on the side of the fixture can be used to select either the fluorescent lamp, the incandescent lamps, or both types of lamps. A convenient wall switch, not shown, can then be used to routinely turn the selected lamp (or lamps) on or off.

This fixture has the advantage of ease of retrofit in many existing bathrooms. Many baths have a fixture over a mirror. The wiring for an old fixture normally can be used for a new fixture. The existing switch or switch holder with new switch can be used for the new fixture. This eliminates the need for expensive wall and wiring modifications.

Another advantage of the fluorescent lamp fixture in the bathroom is the opportunity for exposing large areas of skin while in front of the mirror and while bathing. With large area skin exposure the vitamin D can be formed with an exposure that is a much smaller fraction of an MED. Also the cholesterol over a larger area of the skin is converted to vitamin D and other compounds. In the work environment normally only the head, neck, arms and hands are exposed to the light environment. Only some workplaces have bare tube fluorescent lighting with significant UV-B for vitamin D formation needed in the winter. These workplaces have the disadvantage of providing additional UV-B for those who obtain too much daily solar radiation exposure in the summer. For those with increased weekend exposure, bare tube fluorescent lamp irradiation during the week can improve the day-to-day balance between weekday and weekend exposure.

Ultraviolet B lamp fixture for use over a shower or bathtub

Figure 19:
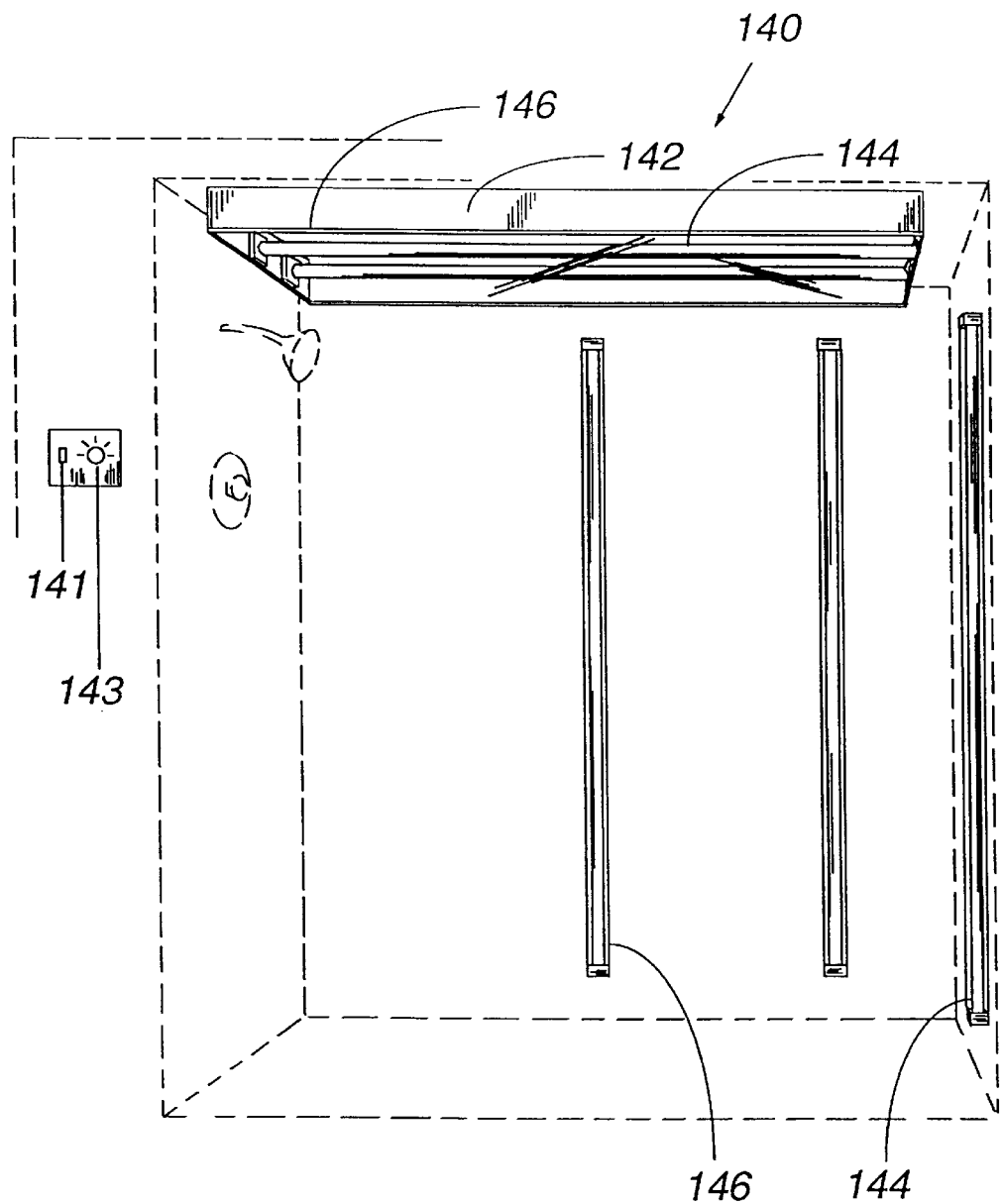
FIG. 19 is a schematic view of fluorescent light fixtures for a shower.

FIG. 19 is a schematic view of a fluorescent lamp fixture, 140, for whole body exposure during bathing. Multiple lamps, 144, are utilized for uniformity of irradiation and sufficient ultraviolet B exposure during the period while in the shower or a tub. A switch, 141, is used to turn the lamps on and a timer, 143, is used to automatically turn the lamps off to avoid overexposure. The lamps are supported in the frame, 142. The frame, 142, is mounted on the walls or ceiling. The lamps, 144, have protective covers, 146, to prevent breakage if bumped and to seal out moisture.

Ultraviolet B lamp fixture for use over a hospital bed

Figure 20:
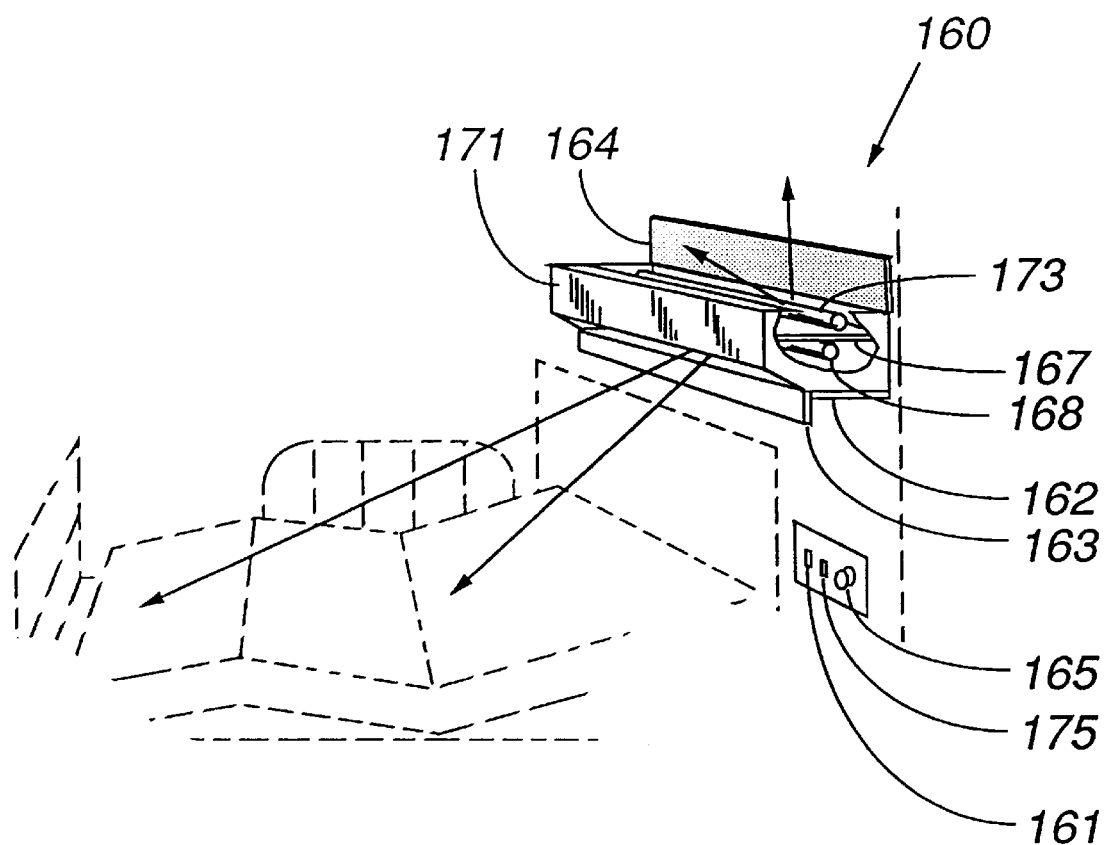
FIG. 20 is a perspective view of a fluorescent lamp fixture for a hospital bed.

FIG. 20 is a perspective view of a fluorescent lamp fixture, 160, for a hospital bed, The lower flap section, 163, can be opened to the position shown for exposure of a patient to the ultraviolet B radiation from the fluorescent lamp, 168. The bed lamp switch, 161, is used to turn the lower bed lamp on. The timer, 165, is used to turn the bed irradiation lamp off to avoid overexposure. The room light switch, 175, turns the upper room illumination lamp, 173, on or off. When the upper diffuser, 164, is rotated up the room irradiation contains ultraviolet B irradiation. When the upper diffuser, 164, is rotated down to cover the upper lamp, 173, the diffuser blocks ultraviolet B radiation. The upper diffuser, 164, transparent to visible light, transmits light for general indirect room lighting when rotated down over the fluorescent lamp.

For patient body exposure to ultraviolet B radiation the lower diffuser, 163, is rotated down to allow passage of the ultraviolet B radiation though the opening as shown in FIG. 20. Following the irradiation period when further ultraviolet B radiation is not needed the lower diffuser, 163, can be rotated up to block the ultraviolet B radiation from the lower lamp, 168, but still transmit visible light for reading and general illumination. The diffuser, 162, provides additional visual light diffuse transmission for reading and illumination.

The opaque baffle, 167, enables the bed and room illumination to be controlled separately using the switches, 161 and 175.

Quartz halogen lamp wall mount fixture

Figure 21:
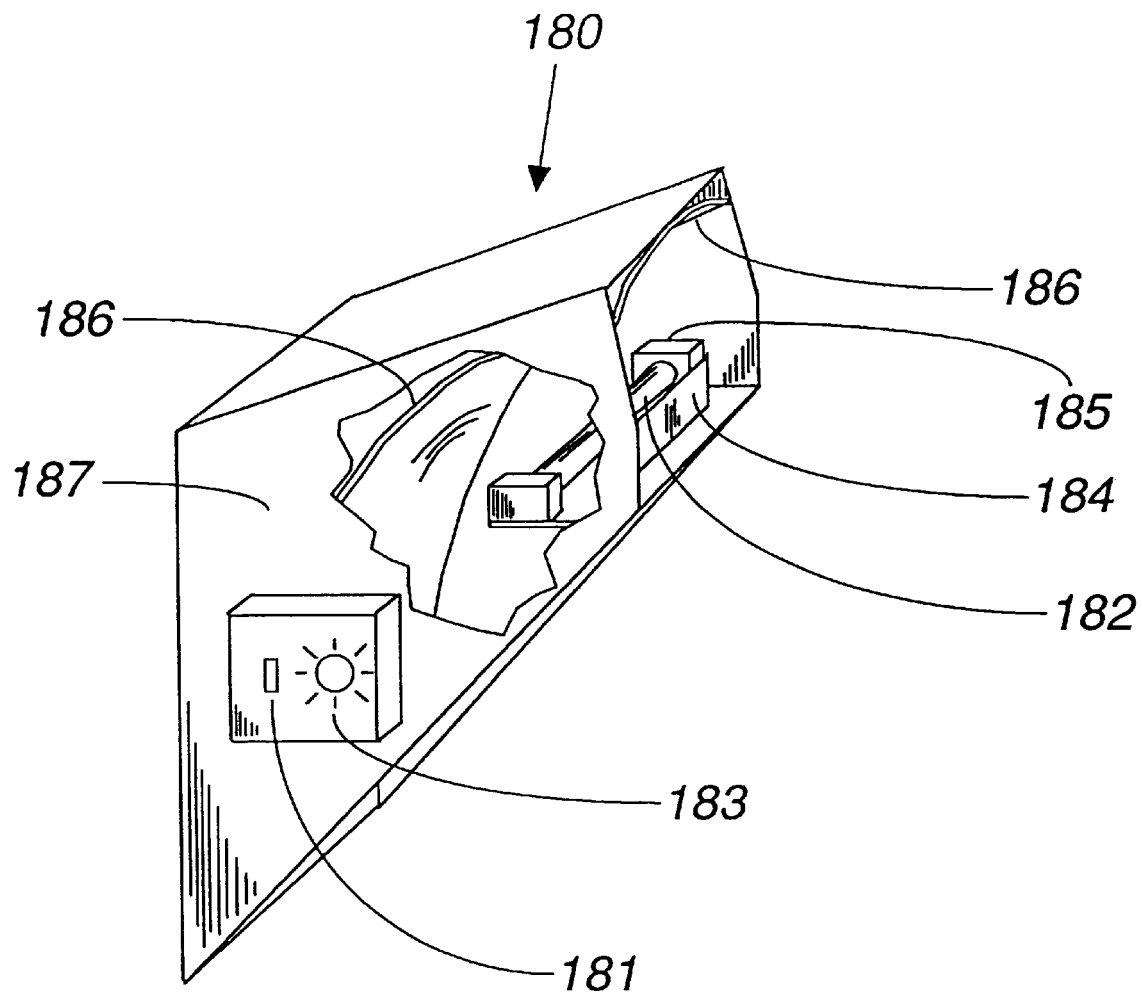
FIG. 21 is a schematic view of a wall mount quartz halogen lamp fixture.

The wall mount fixture, 180, shown in FIG. 21 using a quartz halogen lamp, 182, is smaller than the fluorescent lamp fixture, 160, of FIG. 20 for convenience for home use over a bed or other area.

The lamp can be turned on using the switch, 181. A timer, 183, is used to turn the unit off to reduce the risk of overexposure. A shield, 184, is used to shade the small bright source to reduce the possibility of eye damage and for general visual comfort. The reflector, 186, directs the light toward the exposure area.

The wall mount fixture, 180, shown in FIG. 21 using a quartz halogen lamp, 182, is smaller than the fluorescent lamp fixture, 160, of FIG. 20 for convenience for home use over a bed or other area.

The lamp can be turned on using the switch, 181. A timer, 183, is used to turn the unit off to reduce the risk of overexposure. A shield, 184, is used to shade the small bright source to reduce the possibility of eye damage and for general visual comfort. The reflector, 186, directs the light toward the exposure area.

Figure 22:
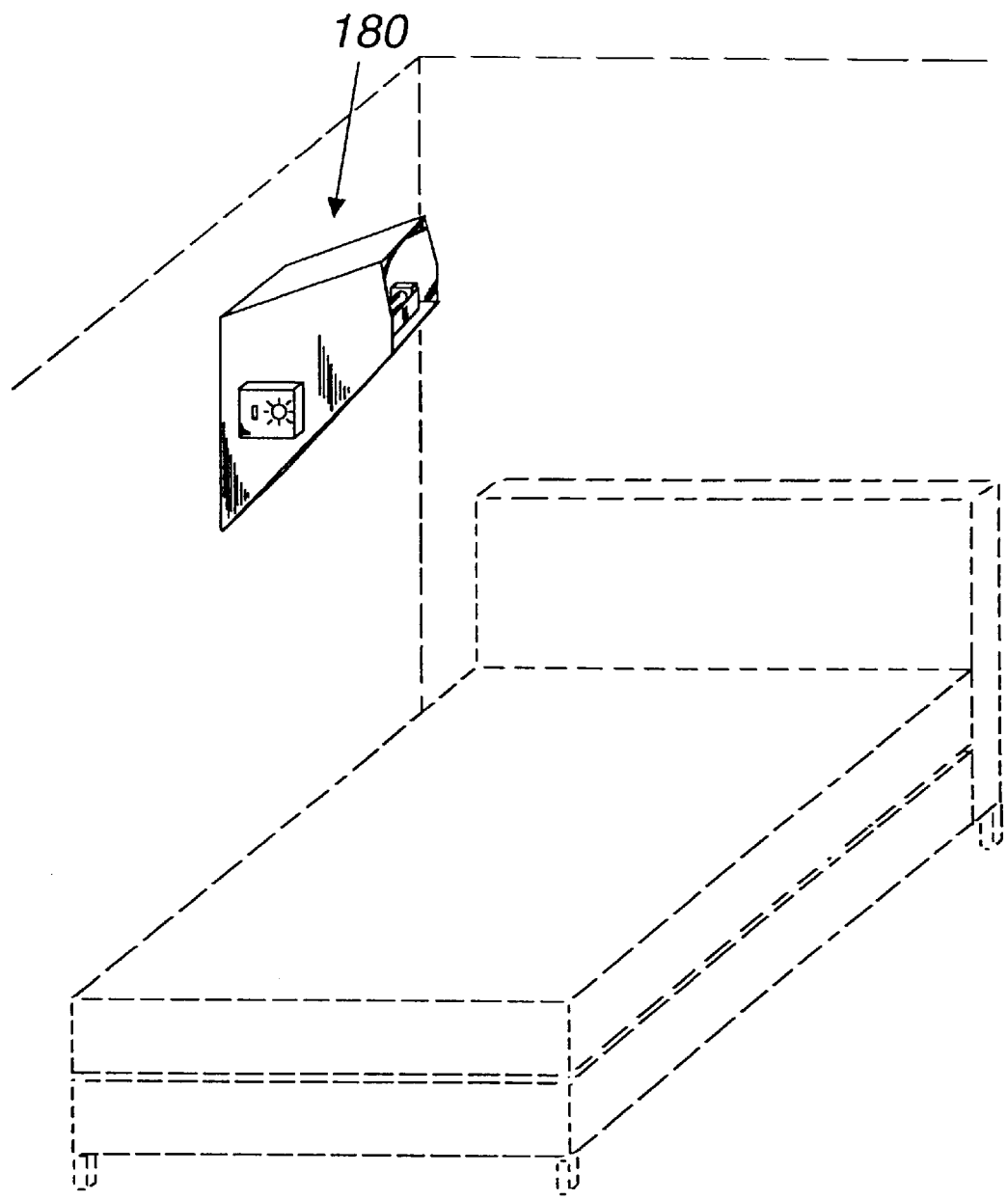
FIG. 22 is a schematic view of the FIG. 21 wall mount fixture over a bed.

The internal components of the wall mount fixture, 121, shown in FIG. 22 include a support, 188, the reflector, 186, the quartz halogen lamp, 182, the lamp holders, 185, and the lamp shield, 184. Electrical wires for the lamp and switch are not shown. For higher irradiances the lamp can be replaced by a mercury lamp.

The use of a bed for skin exposure enables a person to use both the supine and prone positions to expose both the front and back. Most chairs enable front exposure but are not suitable for exposure of much of the back area.

Device for exposure during exercise

Figure 23:
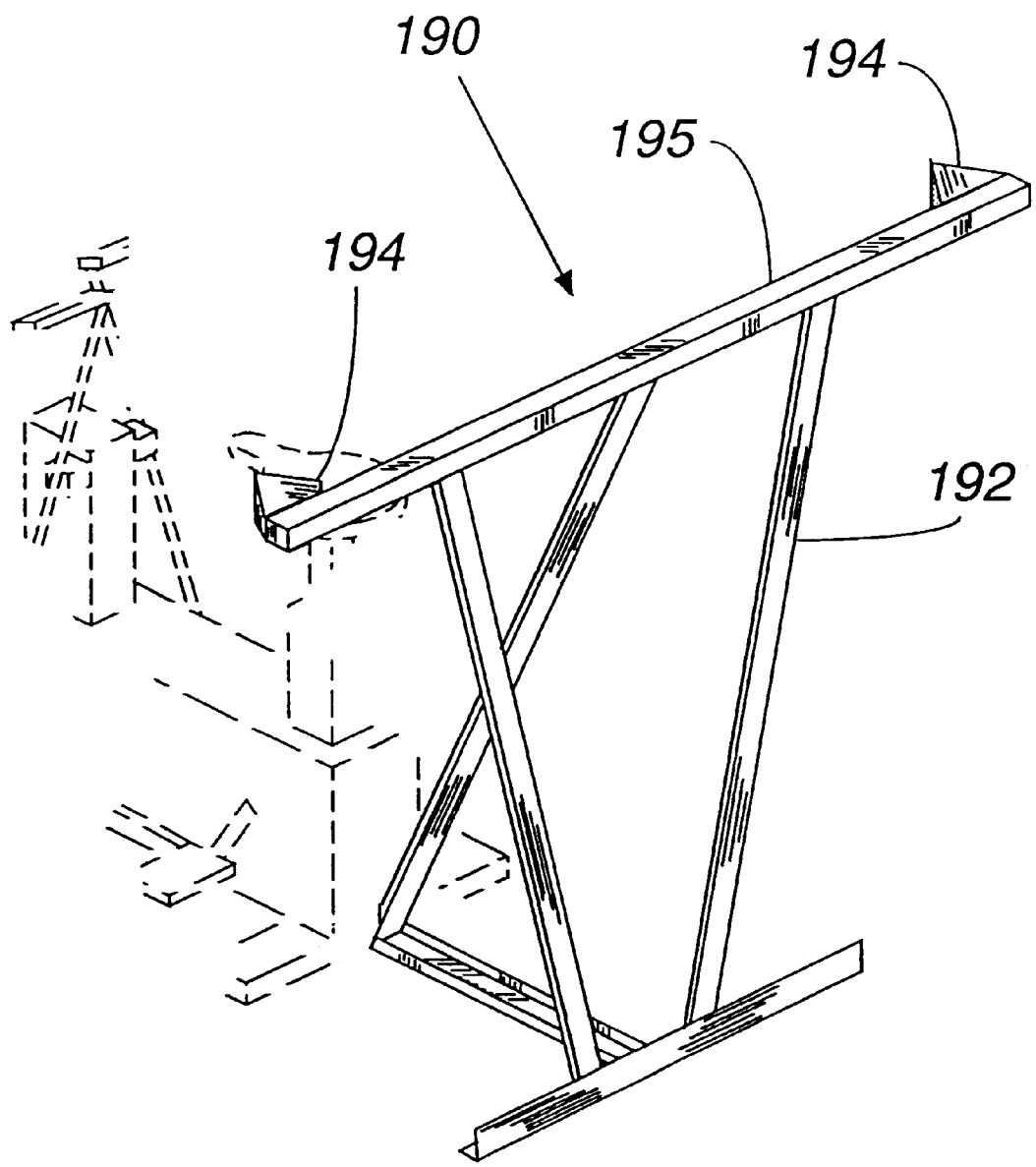
FIG. 23 is a schematic view of a lighting device for exposure of an individual during exercise periods.

FIG. 23 is an exercise cycle with lamps for exposure during exercise. The greater blood flow during exercise enables more of the body blood pool to circulate to areas near the skin surface for exposure during the exercise period. This provides winter indoor exercise conditions closer to the outdoor summer exercise environment. The device, 190, includes a base, 212, base supports, 202, a seat, 220, movable seat support, 198, fixed seat support, 196, handle pivot support, 219, handle pivot, 224, handles, 218, handle linkage 214, foot pedals, 204, pedal linkage, 206, pedal crank, 208, light bar, 195, light bar supports, 192, and lights, 194. The foot motion and seat arrangement provide exercise similar to riding a bicycle. The handle motion provides hand and arm movements similar to movements during running. The lamp, 194, provides irradiation similar to the sun being above and behind the individual. A timer, not shown, is used to control the exposure period to prevent overexposure.

The seat, 191, can be positioned at different heights using the movable seat support, 198, to accommodate persons with different leg lengths. The light arrangement provides irradiation of legs and arms in addition to the back. The use of lights attached to the exerciser enables exposure control with repeatable exposures on different days in comparison with non-attached lights without effective control of the lamp to subject distance. The use of shorts and short sleeve garments during exercise allows exposure of arms and legs. This enables vitamin D generation at low exposure doses. The exposure can reduce the cholesterol in the skin of the arms and legs. Repeated use of the lamp exposure over long periods of time along with avoidance of dietary excesses of cholesterol can reduce arterial plaque and reduce high blood pressure, Kime, 34.

REFERENCES

A. U.S. PATENT DOCUMENTS

| | | | |
|---|---|---|---|
| 1. | 4,546,493 | 9/1982 | Bortnick (Tan through wearing apparel) |
| 2. | 4,656,778 | 10/1986 | Fiorenza (Storm window assembly) |
| 3. | 5,206,229 | 4/1987 | Calverley et al. (Vitamin D analogues) |
| 4. | 5,196,705 | 2/1990 | Ryan (Sun exposure monitoring device) |
| 5. | 4,843,279 | 6/1987 | Rattray (Fluor. lamp approx. sunlight UV spectrum) |
| 6. | D282,581 | 6/1983 | Pepall (Sun lamp) |
| 7. | 5,000,444 | 5/1988 | Dalebout (Dual action exercise cycle) |
| 8. | D310,878 | 6/1988 | Young (Combined tanning and exercise station) |

B. Other Publications
9. Ainsleigh, H. G.: Beneficial effects of sun exposure on cancer mortality. Prev. Med. 22:132–140;1993.
10. Altschul, M. U.: Inhibition of experimental cholesterol arteriosclerosis by ultraviolet irradiation. NEJM: 249:96–99;1953.
11. Anderson, John J. B. and Svein U. Toverud: Diet and vitamin D: A review with an emphasis on human function. J. Nutr. Biochem. 5, 58–65; 1994.
12. Apperly, F. L.: The relation of solar radiation to cancer mortality in North America. Cancer Res. 1:191–195;194.
13. Avioli, L. V.: Significance of osteoporosis: a growing international health care problem. Calif. Tissue Int. 49:Suppl. 1, s5–s7;1991.
14. Bayard, F., Philippe Bec and J. Pierre Louvet: Measurement of plasma 25-hydroxychoecaliferol in man. Europ. J. Clin. Invest. 2:195–198; 1972.
15. Bell, N. H.: Endocrine complications of sarcoidosis. Endrocrinol. Metab. Clin. North Am. 20: 645–654; 1991.
16. Blask, David E. Melatonin in oncology. Chapter 17 in Melatonin: Biosynthesis, Physiological effects, and Clinical Applications Edited by Hing-Sing Yu and Russel J. Reiter. CRC Press Boca Raton, Fla. 1993.
17. Brunvand, Lief and Haug Egil: Vitamin D deficiency amongst Pakistani women in Oslo. Acta Obstet. Gynecol. Scan. 72: 264–268; 1993.
18. Berger, D. S.: Specifications and design of solar simulators. J. Invest. Dermatol. 53:192–199; 1969.
19. Cebula T. A., Henrikson E. N., Hartman P. E., and Biggley W. H.: Reversion profiles of fluorescent light compared with far ultraviolet: homologies and differences. Photochem. and Photobio. 61: 353–359; 1995.
20. Dale, Abbie. E. and Miriam E. Lowenberg: Consumption of vitamin D in fortified and natural foods and in vitamin preparations. Jour. of Pediatrics 70: 952–955; 1967.
21. Davies, D. M.: Calcium in healthy men deprived of sunlight. Annals New York Acad. Sci. 453:21–27;1985.
22. Diffey, B. L. and P. J. Saunders: Behavior outdoors and its effect on personal ultraviolet exposure rate measured using an ambulatory datalogging dosimeter. Photochem and Photobio 61:615–618; 1995.
23. Driscoll, W. G., Editor: Handbook of Optics, Optical Society of America, McGraw Hill Company, New York, 1978. pages 7–24 and 8–32.
24. FDA 72 100: Scientific literature reviews on generally recognized as safe (GRAS) food ingredients, vitamin D. Tracor-Jitco Inc. July 1974. NTIS PB 234 901.
25. FDA/BF-79/70: Evaluation of the health aspects of vitamin D2 and vitamin D3 as food ingredients. Fed of Am Societies for Exp. Biology, Bethesda, Md. PB-293 099. 1978.
26. Fotiades, J., N. A. Soter, et al.: A three year follow-up evaluation on 28 HIV-positive patients treated with ultraviolet B (UVB) phototherapy. J. Invest. Dermatol. 104:660; 1995.
27. Fraser, D R: Vitamin D. Lancet 345:104–107;1995.
28. Frederick, J. E. and Carynelisa Erlick: Trends and Interannual variations in erythemal sunlight, 1978–1993. Photochemistry and Photobiology 62:476–484; 1995.
29. Garland, C. F. et al: Geographical variation in breast cancer mortality in the United States: A hypothesis involving exposure to solar radiation. Prev. Med. 19: 614–622; 1990.
30. Garland, Cedric F., Frank C. Garland et al.: Colon cancer parallels rickets. pages 81–111 in: Calcium, Vitamin D and Prevention of Colon Cancer 1990. Edited by M. Lipkin, H. L. Newmark and G. Kelloff. CRC Press, Boco Raton, Fla.
31. Goettsch, W. et al.: Effects of in vitro exposure to ultraviolet radiation on the functional activity of lymphocytes with emphasis on susceptibility of different species. Photochem. Photobio. 60: 373–379; 1994.
32. Goldsmith, L. A., Physiology, Biochemistry, and Molecular Biology of the Skin. 2nd Ed. Oxford University Press 1991, p929.
33. Golier, Julia A. Peter M. Marzuk, et al.: Lower serum cholesterol level and attempted suicide. Am. J. Psychiatry 152:419–423;1995.
34. Gould, A. Lawrence, Jacques E. Rossouw et al.: Cholesterol reduction yields clinical benefit. Circulation 91:2274–2282; 1995.
35. Harber, L. C.: Abnormal responses to ultraviolet radiation: drug-induced photosensitivity. In: Dermatology in General Medicine, Ed. by Fitzpatrick et al. McGraw-Hill Inc. New York Fourth Edition, 1993.
36. Harrison, Simone et al.: Sun exposure and melanocytic naevi in young Australian children. Lancet 344: 1529–1532; 1994.
37. Hawk, J. L. M. and Norris, P. G.: Abnormal responses to ultraviolet radiation: idiopathic. In: Dermatology in General Medicine, Ed. by Fitzpatrick et al. McGraw-Hill Inc. New York Fourth Edition, 1993.
38. Heaney, R. P.: Calcium and vitamin D in human nutrition. In Calcium, Vitamin D and Colon Cancer. Ed. by M. Lipkin, H. L. Newmark and G. Kelloff, CRC Press, Boco Raton, 1991.

39. Holloway, L.: Atmospheric sun protection factor on clear days: It's observed dependence on solar zenith angle and its relevance to the shadow rule fo rsun protection. Photochem. and Photobio. 56:229–234; 1992.
40. Jacobus, Claire H., Holick, M. F. et al.: Hypervitaminosis D associated with drinking milk. New Engl. J. of Med. 326:1173–1177; 1992.
41. Kato, M, Honma, K, et al. Effects of exposure to a circularly polarized 50-Hz magnetic field on plasma and pineal melatonin levels in rats. Bioelectromagnetics 14: 97–106; 1993.
42. Kime, Z. R.: "Sunlight"; World Health Publications, Penryn, Calif. (1980).
43. Knox, E. G.: Ischemic-heart-disease mortality and dietary intake of calcium. Lancet 1, 1465–1467;1973.
44. Kovacs, R.: Light Therapy. Publisher, Charles C Thomas, Springfield, Ill. 1950. p96.
45. Kummerow, F. A.: Nutrition imbalance and angiotoxins as dietary risk factors in coronary heart disease. Am J Clin Nutr 32:58–83; 1979.
46. Leach, J. F., McLeod, V. E. et al.: Measurement of the ultraviolet doses received by office workers. Clin. and Exp. Dermatol. 3:77–79;1978.
47. Lefkowitz, Ellen S, and Cedric F. Garland: Sunlight, vitamin D, and ovarian cancer mortality rates in US women. Internat. Jour. Epidemiology 23:1133–1136;1994.
48. Licht, S.: History of ultraviolet therapy. In: Therapeutic Electricity and Ultraviolet Radiation. Third Edition Ed. by G. K. Stillwell, Williams and Wilkins, Baltimore. 1983.
49. Linden, V.: Vitamin D and myocardial infarction. Br Med Jour 3:647–650;1974.
50. Loomis, W. F.: Skin-pigment regulation of vitamin-D biosynthesis in man. Science 157:501–506; 1967
51. Lubani M. M., al-Shab T. S. et al., Vitamin-D-deficiency rickets in Kuwait, the prevalence of a preventable disease. Ann. Trop. Pediatric. September 9 (3) 134–9; 1989.
52. Lund, B. and Sorensen, 0. H.: Measurement of 25-hydroxyvitamin in serum and its relation to sunshine, age and vitamin D intake in the Danish population. Scand. J. clin. Lab. Invest. 39:23–30;1979.
53. Lytle, C. D., Cyr, W. H., et al.: An estimation of squamous cell carcinoma risk from ultraviolet radiation emitted by fluorescent lamps. Photodermatol. Photoimmunol. and Photomed. 9:268–274; 1993.
54. Mangus, K. (Ed.) Incidence Trends in the Nordic Countries: Effects of Sun Exposure. In: Trends in Cancer Incidence, Causes and Practical Implications. New York: Hemisphere Publication Corporation pp 387–392; 1982.
55. Mason, T. J., J. F. Fraumeni, et al.: An Atlas of Mortality from Selected Diseases, U.S. Department of Health and Human Services, NIH publication No. 81-2397, May 1981.
56. Maxwell K. J and Elwood J. M.: Could melanoma be caused by fluorescent light? A review of the relevant physics. In Recent Results in Cancer Research, vol. 102. Springer-Verlag, Berlin, New York, 1986. p. 137–143.
57. McDonagh, A. F. and Lightner, D. A.: Phototherapy and the Photobiology of Bilirubin. Seminars in Liver Disease 8: 272–283; 1988.
58. Neer, R. M.: Environmental Light: Effects on vitamin D Synthesis and Calcium Metabolism in Humans. Annals New York Acad. Sci. 453:17; 1985.
59. Nieves J., F. Cosman, J. Herbert, V. Shen, and R. Lindsay: High prevalence of vitamin D deficiency and reduced bone mass in multiple sclerosis. Neurology, September 1994, 44:1687–1692.
60. Nowak, M. A. and McMichael, A. J.: How HIV Defeats the Immune System. Sci. Am 273:58–65; 1995.
61. Oppe, T. E.: Infantile hypercalcaemia, nutritional rickets, and infantile scurvy in Great Britain. Br. Med. J. 1: 1659–1661; 1964.
62. Parkin, D. M. et al. Eds.: Cancer Incidence in five Continents. World Health Organization. Scientific Publication No. 120, Lyon, 1992.
63. Parrish, J. A, Jaenicke, K. F., and Anderson, R. R.: Erythema and melanogenesis action spectra of normal human skin. Photochem. and Photobio. 36:187–191;1982.
64. Pennington, Jean A. T.: Food values of portions commonly used. 15th Edition. J. B. Lippincott Company, Philadelphia, 1989.
65. Pincussen, L.: Effect of ultraviolet and visible rays on carbohydrate metabolism. Arch. Phys. Therapy, X-ray, Radium 18:750–755;1937.
66. Prentice, Ann: Calcium intakes and bone densities of lactating women and breast-fed infants in The Gambia. Advances in Exp. Med. and Biology: 352:243–255; 1994.
67. Reed, P. B.: Nutrition; West Publishing Company, St. Paul, 1980. p. 315.
68. Schreck, S., Panozzo, J. et al: The effects of multiple UV exposures on HIV-LTR expression. Photochem. and Photobio. 61:378–382; 1995.
69. Scott, B. O.: Clincial uses of ultraviolet radiation. In: Therapeutic Electricity and Ultraviolet Radiation. Ed by Stillwell, G. K. 3rd edition. Williams & Wilkins Baltimore/London. 1983.
70. Scragg, R., Jackson, R., et al.: Myocardial Infarction is Inversely Associated with 25-Hydroxyvitamin D3 Levels: A Community-Based study. Internat. J. of Epidemiol. 19:559–563; 1990.
71. Shigenaga, M. K. and Ames, B. N.: Oxidants and mitogenesis as causes of mutation and cancer: The influence of diet. In: Antimutagenesis and Anticarcinogenesis Mechanisms III. Ed. by G. Bronzetti, H. Hayatsu, et al. Plenum Press, New York. 1993. p 426–427.
72. Siegel, Mary Ellen: Safe in the Sun. Walker & Company, New York, 1990.
73. Sliney, D. and Wolbarsht, M: Safety with Lasers and Other Optical Sources. Plenum Press, New York, 1980. page 495.
74. Stamp, T. C. B. and Round, J. M.: Seasonal changes in human plasma levels of 25-Hydroxyvitamin D. Nature 247:563–565; 1974.
75. Stanley, S. K. et al.: Induction of expression of human immunodeficiency virus in a chronically infected promonocytic cell line by ultraviolet irradiation. AIDS Res. Hum. Retrovirsuses 5: 375–384;1989.
76. Sterns, Genevieve: Early studies of vitamin D requirement during growth. Am. J. Public Health 58:2027–2042;1968.
77. Studzinski, G. P. and Dorothy C. Moore: Sunlight—can it prevent as well as cause cancer? Cancer Research 55:4014–4022;1995.
78. Valerie, K. et al.: Activation of human immunodeficiency virus type 1 by DNA damage in human cells. Nature 333: 78–81; 1988.
79. Vieth, R: The mechanism of vitamin D toxicity. Bone and Mineral, 11:267–272; 1990.
80. Vincek, V.: Sunlight induced progression of AIDS. Medical Hypotheses 44:119–123; 1995.
81. Waksman, B. H.: More genes versus environment. Nature, 377:105–106;1995.
82. Webb, A. R., and Holick, M. F. (1988). Influence of season and latitude on the cutaneous synthesis of vitamin D3: Exposure to winter sunlight in Boston and Edmonton will not produce vitamin D3 synthesis in human skin. J. Clin. Endocrinol. Metab. 67, 373–378.
83. Westerhof, W., Estevez-Uscanga, Oscar et al.: The relation between constitutional skin color and photosensitivity estimated from UV-induced erythema and pigmentation dose-response curves. J. Invest. Determatol. 94:812–816; 1990.
84. Williams, Sue R.: Essentials of Nutrition and Diet Therapy. 6th Edition. Mosby, St. Louis, 1994.
85. World Health Organization (WHO). Environmental Health Criteria 160, Ultraviolet Radiation. Geneva 1994.
86. World Health Organization (WHO). 1993 World Health Statistics Annual. Geneva 1994.

What is claimed is:

1. A skylight comprising: a skylight body portion; means on said body portion for mounting said skylight upon a ceiling; said skylight body portion supporting an element which transmits infrared, visible and ultraviolet solar radiation; at least one light transmissive blocking element mounted in said skylight which blocks UV-B radiation whereby it is movable between a position entirely blocking said elements and a position allowing the element to transmit al radiation; and means for moving said blocking element relative to said transmitting element to a variety of positions to control the amount of radiation emanating from the skylight.

2. A skylight according to claim 1 wherein said skylight includes at least one fixed blocking element which blocks UV-B radiation vertically spaced from said movable blocking element.

3. A skylight according to claim 2 wherein the means for moving said blocking element comprises a lead screw.

4. A skylight according to claim 3 wherein said lead screw includes a rider which is connected to said blocking element and enables said blocking element to be movable relative to said skylight and said transmitting element.

* * * * *